United States Patent [19]

Hannum et al.

[11] Patent Number: 5,075,222
[45] Date of Patent: Dec. 24, 1991

[54] INTERLEUKIN-1 INHIBITORS

[75] Inventors: Charles H. Hannum; Stephen P. Eisenburg; Robert C. Thompson, all of Boulder; William P. Arend; Fenneke G. Joslin, both of Denver, all of Colo.

[73] Assignee: Synergen, Inc., Boulder, Colo.

[21] Appl. No.: 506,522

[22] Filed: Apr. 6, 1990

Related U.S. Application Data

[63] Continuation of Ser. No. 266,531, Nov. 3, 1988, abandoned, which is a continuation-in-part of Ser. No. 248,521, Sep. 23, 1988, abandoned, which is a continuation-in-part of Ser. No. 238,713, Aug. 31, 1988, abandoned, which is a continuation-in-part of Ser. No. 199,915, May 27, 1988, abandoned.

[51] Int. Cl.$^5$ .............. C12P 21/02; C12P 19/34; C12N 15/00; C12N 7/00; C12N 5/00; C12N 1/21; C12N 15/70; C12N 15/79; C12N 15/81; C12N 1/16; C07H 15/12; C07K 3/00

[52] U.S. Cl. .................. 435/69.1; 435/91; 435/172.3; 435/235.1; 435/240.2; 435/252.3; 435/320.1; 435/255; 435/252.33; 530/27; 530/350; 935/18; 935/29; 935/31; 935/32; 935/34; 935/38; 935/56; 935/57; 935/62; 935/70; 935/72

[58] Field of Search .............. 435/69.1, 91, 172.3, 435/253.33, 320, 235; 536/27; 530/350; 935/4, 18, 29, 32, 34, 38, 56, 57, 62, 70, 72, 77, 82, 320.1, 240.1, 255

[56] References Cited

FOREIGN PATENT DOCUMENTS

WO89/01946  3/1989  PCT Int'l Appl.

OTHER PUBLICATIONS

Roberts, N. J. et al., J. Exp. Med., vol. 163, pp. 511–519 (1986).
Mariahs, T. et al., Molecular Cloning, A Laboratory Manual Cold Spring Harbor Laboratory, CSH, N.Y. (1982).
Helfman, D. M. et al., Proc Natl. Acad Sci USA, vol. 80, pp. 31–35 (1983).
Suggs, S. V. et al., Proc Nat'l Acad Sci USA, vol. 78, pp. 6613–6617 (1981).
Seckinger et al., The Journal of Immunology, 139:1546–1549 (1987).
Seckinger et al., 18th Forum in Immunology, pp. 486–488.
Billingham et al., British Journal of Rheumatology, 24 (suppl. 1):25–28 (1985).
Pujol et al., Life Sciences, 41:1187:1198 (1987).
Tan et al., Australian and New Zealand Rheumatism Associations, Abstract, 113, (1986).
Seckinger et al., The Journal of Immunology, 139:1541–1545 (1987).
Bories et al., Biochemical and Biophysical Research Communications, 147:710–715 (1987).
Arend et al., The Journal of Immunology, 134:3868–3875 (1985).
Hannum et al., Nature, 343:336–340 (1990).
Maniatis et al., Molecular Cloning, A Laboratory Manual, Cold Spring Harbor Laboratory (1982), pp. 387–388.
Furutani et al., Nucleic Acids Research, 13:5869–5882 (1985).
Kramer et al., Cell, 30:599–606 (1982).
Rosenstreich et al., J. Exp. Med., 168:1767–1779 (1988).

*Primary Examiner*—Richard A. Schwartz
*Assistant Examiner*—Joan Ellis
*Attorney, Agent, or Firm*—Finnegan, Henderson, Farabow, Garrett & Dunner

[57] ABSTRACT

DNA sequences that encode Interleukin-1 inhibitors and recombinant-DNA methods for the production of interleukin-1 inhibitors are provided. The DNA sequences encode proteins having interleukin-1 inhibitors activity.

31 Claims, 22 Drawing Sheets

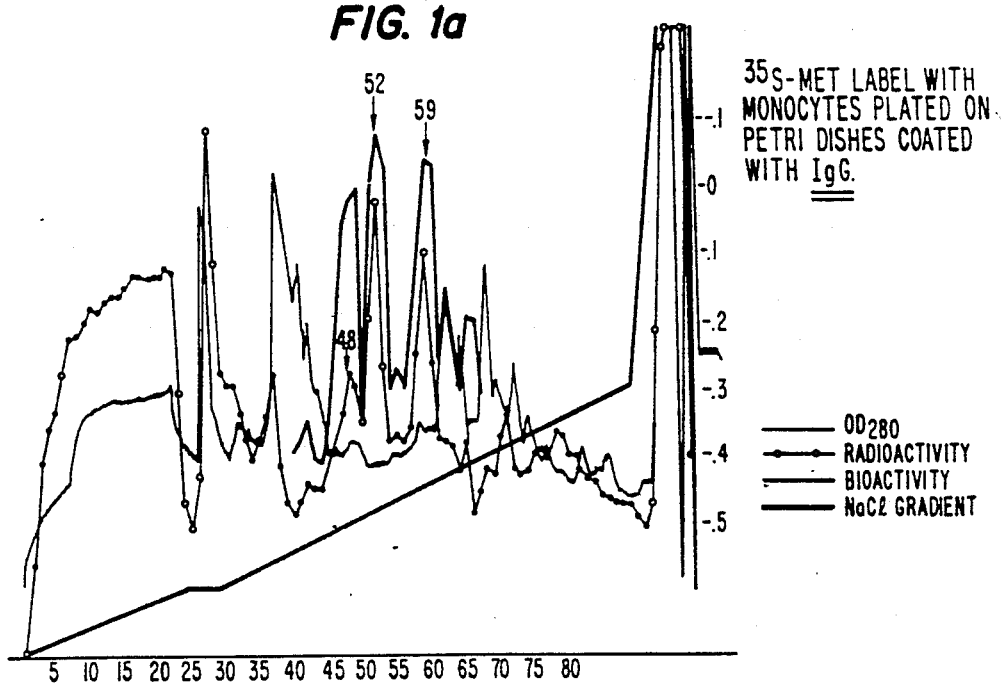
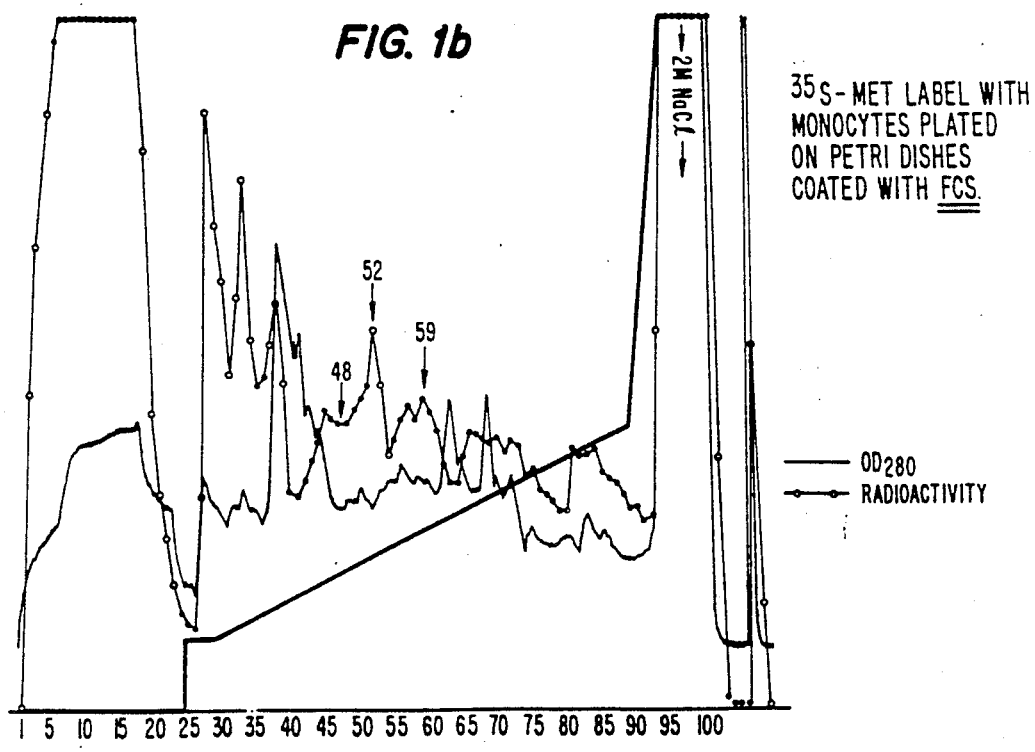

AUTORADS

SILVER-STAINED GELS

AUTORAD

CONSECUTIVE SUPEROSE 12 (SIZING) CHROMATOGRAPHIC SEPARATIONS ON MONO Q PURIFIED IL-1j

RERUN FRACTIONS 37+38

— OD$_{280}$
—o— RADIOACTIVITY
—•— BIOACTIVITY

FIG. 5a

WESTERN ANALYSIS OF IMMUNOGEN (MONO Q-PURE IL-1$_i$) USING NORMAL MOUSE SERUM (NMS) AND A MIX OF ANTISERA FROM ALL 5 MICE

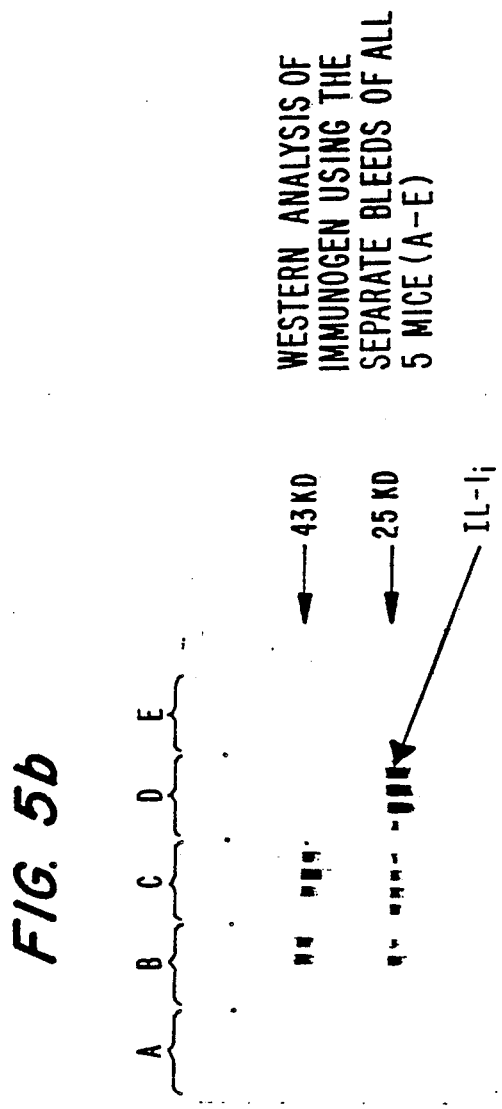

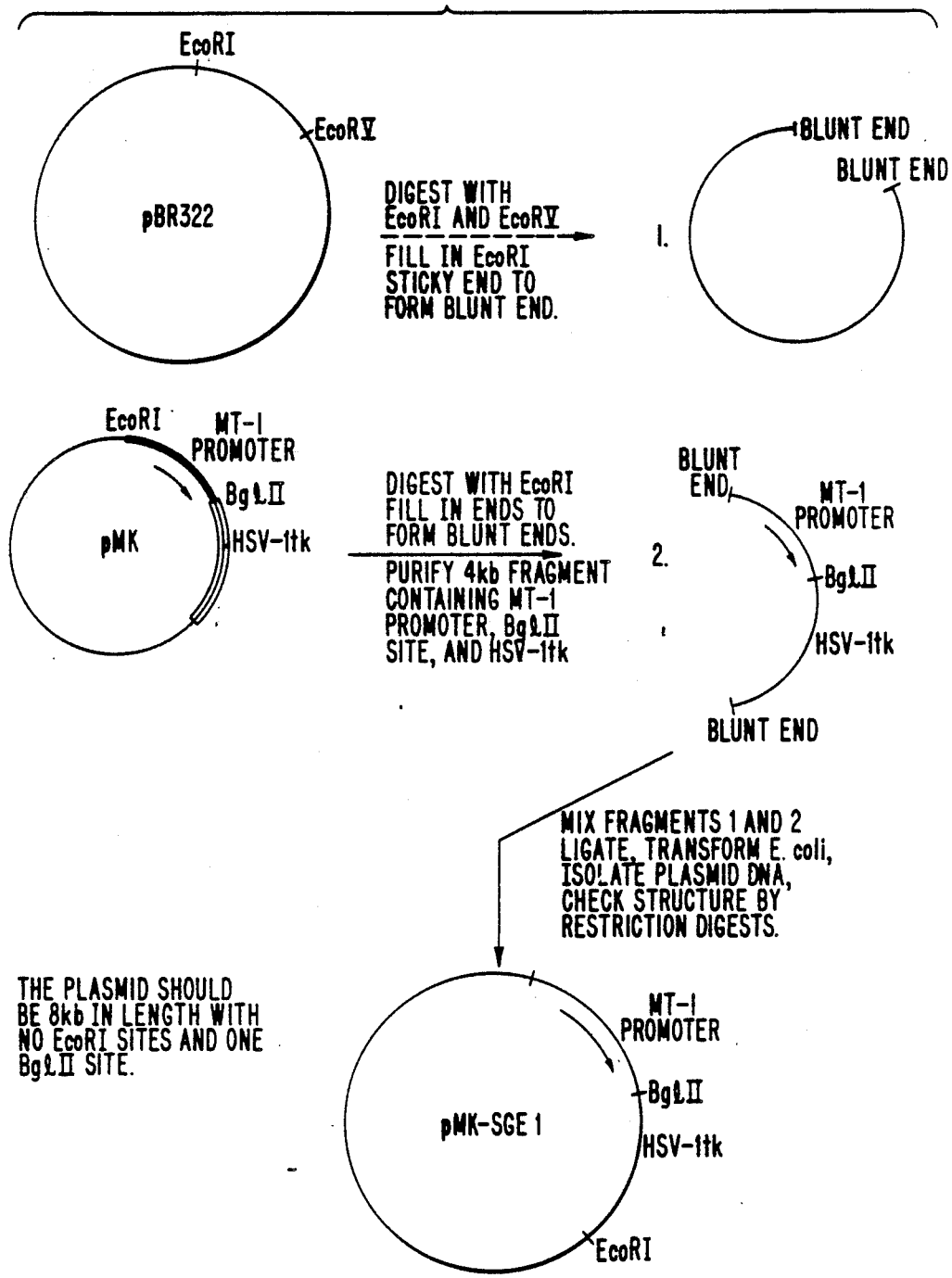

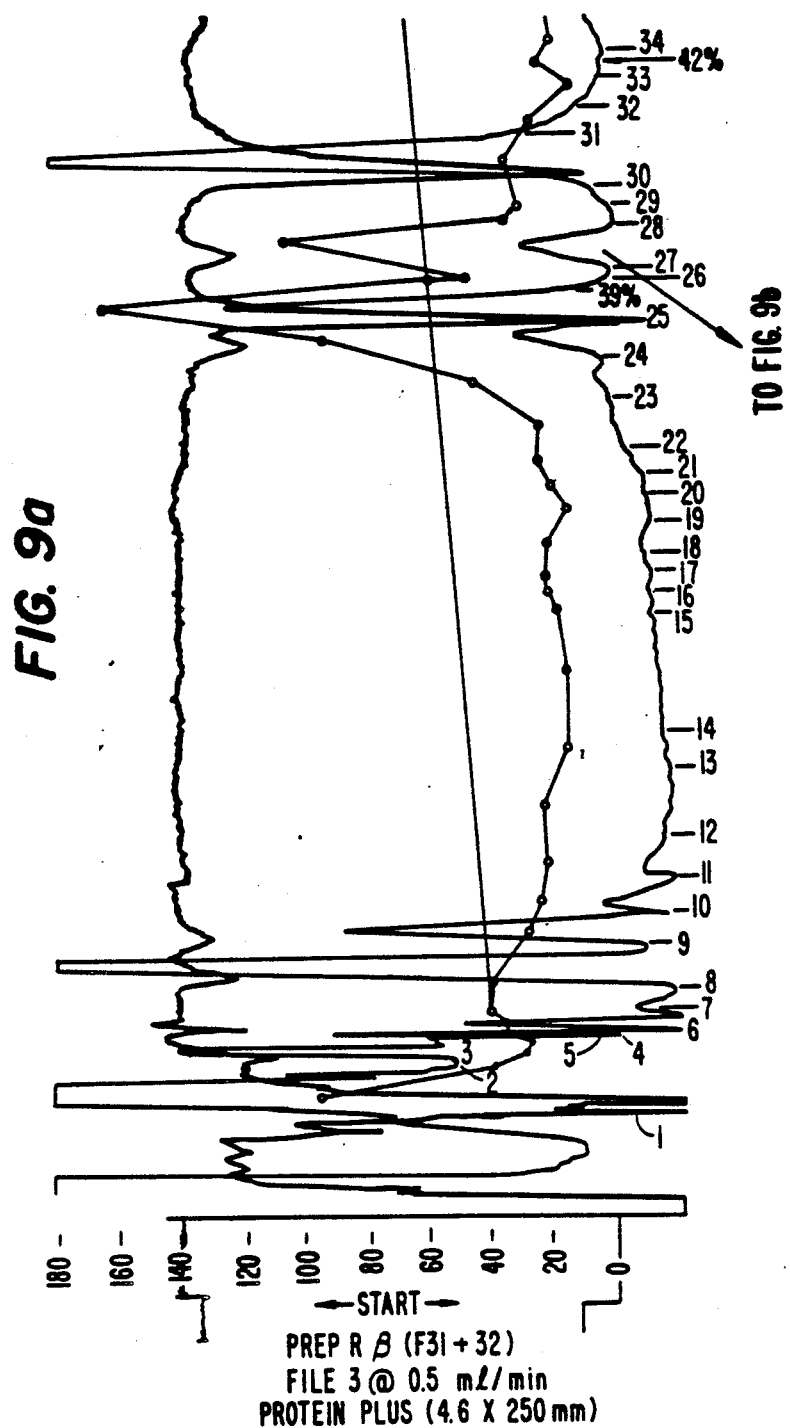

LANE 5 6 8 10 12 14

FIG. 13

```
                              27                                                        54
GCG TCA CAG AAT GGA AAT CTG CAG AGG CCT CCG CAG TCA CCT AAT CAC TCT CCT
Ala Ser Gln Asn Gly Asn Leu Gln Arg Pro Pro Gln Ser Pro Asn His Ser Pro.

81                                                       108
CCT CTT CTG ATC ATT CAG AGA CCG ATC TGC CCA CCC TCT GGG AGA AAA TCC AGC
Pro Leu Leu Ile Ile Gln Arg Pro Ile Cys Pro Pro Ser Gly Arg Lys Ser Ser 135                                                       162
AAG ATG CAA GCC TTC AGA ATC TGG GAT GTT AAC CAG AAG ACC TTC TAT CTG AGG
Lys MET Gln Ala Phe Arg Ile Trp Asp Val Asn Gln Lys Thr Phe Tyr Leu Arg 189                                                       216
AAC AAC CAA CTA GTT GCT GGA TAC TTG CAA GGA CCA AAT GTC AAT TTA GAA GAA
asn Asn Gln Leu Val Ala Gly Tyr Leu Gln Gly Pro Asn Val Asn Leu Glu Glu 243                                                       270
AAG ATA GAT GTG GTA CCC ATT GAG CCT CAT GCT CTG TCT TGG GAA TCC ATG GAG
Lys Ile Asp Val Val Pro Ile Glu Pro His Ala Leu Ser Trp Glu Ser MET Glu
```

FIG. 14

```
         10         20    ↓    30         40         50         60
GAATTCCGGGCTGCAGTCACAGAATGGAAATCTGCAGAGGCCTCCGCAGTCACCTAATCA
                          M  E  I  C  R  G  L  R  S  H  L  I 70         80         90        100        110        120
CTCTCCTCCTCTTCCTGTTCCATTCAGAGACGATCTGCCCACCCTCTGGGAGAAAATCCA
 T  L  L  L  F  L  F  H  S  E  T  I  C (P) P  S  G  R  K  S 130        140        150        160        170        180
GCAAGATGCAAGCCTTCAGAATCTGGGATGTTAACCAGAAGACCTTCTATCTGAGGAACA
 S  K  M  Q  A  F  R  I  W  D  V  N  Q  K  T  F  Y  L  R  N 190        200        210        220        230        240
ACCAACTAGTTGCTGGATACTTGCAAGGACCAAATGTCAATTTAGAAGAAAAGATAGATG
 N  Q  L  V  A  G  Y  L  Q  G  P  N  V  N  L  E  E  K  I  D 250        260        270        280        290        300
TGGTACCCATTGAGCCTCATGCTCTGTTCTTGGGAATCCATGGAGGGAAGATGTGCCTGT
 V  V  P  I  E  P  H  A  L  F  L  G  I  H  G  G  K  M  C  L 310        320        330        340        350        360
CCTGTGTCAAGTCTGGTGATGAGACCAGACTCCAGCTGGAGGCAGTTAACATCACTGACC
 S  C  V  K  S  G  D  E  T  R  L  Q  L  E  A  V  N  I  T  D 370        380        390        400        410        420
TGAGCGAGAACAGAAAGCAGGACAAGCGCTTCGCCTTCATCCGCTCAGACAGTGGCCCCA
 L  S  E  N  R  K  Q  D  K  R  F  A  F  I  R  S  D  S  G  P 430        440        450        460        470        480
CCACCAGTTTTGAGTCTGCCGCCTGCCCCGGTTGGTTCCTCTGCACAGCGATGGAAGCTG
 T  T  S  F  E  S  A  A  C  P  G  W  F  L  C  T  A  M  E  A 490        500        510        520        530        540
ACCAGCCCGTCAGCCTCACCAATATGCCTGACGAAGGCGTCATGGTCACCAAATTCTACT
 D  Q  P  V  S  L  T  N  M  P  D  E  G  V  M  V  T  K  F  Y

550       ↓560        570        580        590        600
TCCAGGAGGACGAGTAGTACTGCCCAGGCCTGCTGTTCCATTCTTGCATGGCAAGGACTG
 F  Q  E  D  E  *
```

INTERLEUKIN-1 INHIBITORS

This application is a continuation of application Ser. No. 07/266,531, filed Nov. 3, 1988, now abandoned, which is a continuation-in-part of Ser. No. 07/248,521, filed Sept. 23, 1988, now abandoned, which is a continuation-in-part of Ser. No. 07/238,713, filed Aug. 31, 1988, now abandoned, which is a continuation-in-part of Ser. No. 07/199,915, filed May 27, 1988, now abandoned.

A. IL-1

Interleukins-1 are a class of proteins produced by numerous cell-types, including monocytes and some macrophages. This class includes at least two 17-18 kilodalton proteins known as interleukin-1 alpha and interleukin-1 beta. These proteins have important physiological effects on a number of different target cells involved in the inflammatory and immune responses. The proteins are co-mitogens (with phytohemaglutinin) for T-cells, cause both fibroblasts and chondrocytes to secrete latent collagenase, and increase the surface adhesive powers of endothelial cells for neutrophils. In addition, they act on the hypothalamus as pyrogens, they stimulate the catabolism of muscle protein, and they cause hepatocytes to synthesize a class of proteins known as "acute phase reactants." Thus, interleukins-1 (IL-1) are obviously an important part of an organism's response to infection and injury.

B. Pathological Roles of IL-1

However, despite their normally teneficial effects, circumstances have come to light in which the actions of IL-1 are harmful. For example, IL-1 may increase the level of collagenase in an arthritic joint and has been implicated as a mediator of both the acute and chronic stages of immunopathology in rheumatoid arthritis. IL-1 may be responsible for altering endothelial cell function, directing the chemotaxis and migration of leukocytes and lymphocytes into the synovial tissue, inducing capillary proliferation and stimulating macrophage accumulation in the synovial lining during the acute phase of this disease. In the phase of tissue destruction, IL-1 has been implicated as a mediator in induction of tissue damage through stimulating release of enzymes from fibroblasts and chondrocytes.

In addition, excessive IL-1 production has been demonstrated in the skin of patients with psoriasis and high levels of IL-1 can be found in the synovial fluid of patients with psoriatic arthritis. IL-1 released by cells in the inflamed synovium in psoriatic arthritis may mediate tissue destruction through stimulation of enzyme release from other cells. The joint pathology of Reiter's syndrome is similar to that seen in psoriatic arthritis and in rheumatoid arthritis. IL-1 has been implicated as a mediator of tissue destruction in these three different forms of inflammatory arthritis. Moreover, IL-1 may be found in the synovial fluid of patients with osteoarthritis. The release of IL-1 by chondrocytes has been implicated in the destruction of articular cartilage in this disease.

IL-1 may also increase the severity of autoimmune diseases. For example, decreased IL-1 production has been described from peripheral blood cells in persons suffering from systemic lupus erythematosus. Moreover, some of the alterations in B lymphocyte function may be related to abnormalities in IL-1 production or IL-1 availability.

Excessive IL-1 production has been demonstrated in the peripheral monocytes of patients with scleroderma, and IL-1 has been implicated as a possible agent of fibrosis through stimulation of collagen production by fibroblasts. The mechanism of tissue damage in dermatomyositis might also involve cell-mediated immunity and IL-1 may therefore be involved as a mediator in this pathophysiological process.

Acute and chronic interstitial lung disease is characterized by excessive collagen production by lung fibroblasts which may be stimulated by IL-1. Recent studies on an animal model of pulmonary hypertension indicate that IL-1 may be responsible for induction of endothelial cell changes that result in narrowing of pulmonary arteries It is this narrowing that leads to pulmonary hypertension and further secondary damage. Thus, IL-1 inhibitors could be useful in treating these lung diseases.

Recent studies have described that IL-1 is capable of directly damaging the beta cells in the Islets of Langerhans that are responsible for the production of insulin. IL-1 damage to the cells is now hypothesized to be a primary event in the acute phase of juvenile diabetes mellitus.

Monocyte and macrophage infiltration in the kidneys predominates in many forms of acute and chronic glomerulonephritis. IL-1 release by these cells may result in local accumulation of other inflammatory cells, eventually leading to inflammatory damage and fibrotic reaction in the kidneys.

It has been demonstrated that the crystals found in tissues or fluids in gout or pseudogout can directly stimulate macrophages to release IL-1. Thus, IL-1 may be an important mediator in the inflammatory cycle in these diseases.

IL-1 is capable of inducing loss of calcium from bones and may be responsible for the osteoporosis that is seen in inflammatory joint diseases.

Keratinocytes from patients with psoriasis release large amounts of IL-1. This mediator may be responsible for the secondary cell proliferation and accumulation which occurs in the skin in patients with this disease.

IL-1 is one of the important endogenous pyrogens and may be responsible for inducing the marked degree of fever seen in some infectious diseases such as acute febrile illnesses due to bacteria or viruses.

Sarcoidosis is characterized by granulomatous lesions in many different organs in the body. IL-1 has been shown to be capable of inducing granuloma formation in vitro and may be involved in this process in patients with sarcoidosis.

Excessive IL-1 production has been demonstrated in peripheral monocytes from both Crohn's disease and ulcerative colitis. Local IL-1 release in the intestine may be an important mediator in stimulating the inflammatory cycle in these diseases.

Certain lymphomas are characterized by fever, osteoporosis and even secondary arthritis. Excessive IL-1 release has been demonstrated by some lymphoma cells in vitro and may be responsible for some of the clinical manifestations of these malignancies. Also, IL-1 production by some malignant lymphocytes may be responsible for some of the fever, acute phase response and cachexia seen with leukemias.

IL-1 release by astrocytes in the brain is thought to be responsible for inducing the fibrosis that may result after damage to the brain from vascular occlusion.

C. Uses for an IL-1 Inhibitor

In these and other circumstances in which IL-1 has a harmful effect, there is clearly a clinical use for an inhibitor of IL-1 action. As IL-1 is a co-mitogen for T-cells, it is central to the development of autoimmune and other immune diseases. Thus, systemically administered, IL-1 inhibitors could be useful immunosuppressive agents. Locally applied, such IL-1 inhibitors could serve to prevent tissue destruction in an inflamed joint and other sites of inflammation. Indeed, to prevent tissue destruction some IL-1 inhibitors could be even more effective when administered in conjunction with collagenase inhibitors.

Therapeutic intervention against the action of IL-1 might be possible at the level of synthesis, secretion, or the target cell's binding or response to the protein. IL-1 is synthesized by monocyte/macrophages and other cells in response to lipopolysaccharides, complement fragments and viruses. Any molecule that blocks binding of these inducing agents to producer cells or which interferes with their effects on the physiology of these cells would serve as a regulator of IL-1 action. IL-1 is not secreted by a traditional secretion system since mRNAs have been isolated that code for at least two 30 kd precursors of the proteins but which do not contain a hydrophobic signal sequence. Release of the active protein from the inactive precursor probably requires proteolysis of that precursor. An inhibitor of the release of IL-1 or IL-ls from their precursors could theoretically regulate IL-1 action. IL-1 probably acts on target cells through a classical receptor-mediated pathway, although that receptor has not yet been isolated. Thus, it could be that a molecule that interferes with IL-1 binding to its receptors, or down-regulates these receptors, could also regulate IL-1 action. Moreover, although the intracellular events following receptor binding of IL-1 are not yet fully understood, it is possible that agents exist that can interfere with the cellular responses to other receptor-mediated events and therefore block IL-1 action. For the reasons stated above, proteins and small molecules capable of inhibiting IL-1 in one or more of these manners have been sought.

Surprisingly, the present inventors have found at least two IL-1 inhibitor proteins with IL-1 inhibiting properties. These molecules have been obtained in a purified form which will enable one of ordinary skill in the art to determine their amino acid sequence. Furthermore, a preparation of cells has been characterized which produce these proteins, and an mRNA that leads to its synthesis has been characterized. Finally, an antisera has been developed that will facilitate screening of cDNA expression libraries for the genes coding for these inhibitors. Together these reagents will allow cDNAs encoding the IL-1 inhibitors to be cloned. These genes will, in turn, make possible the large scale production of IL-1 inhibitors suitable for use in pharmaceutical formulations useful in treating pathophysiological conditions mediated by IL-1.

SUMMARY OF THE INVENTION

This invention relates to IL-1 inhibitors ("IL-li") generally and, more specifically, to a monocyte-derived IL-1 inhibitor. Additionally, the present invention relates to biologically-active analogs of these inhibitors.

An object of the present invention is to provide purified forms of IL-1 inhibitors which are active against IL-1α or IL-1β or a combination thereof. An additional object of the present invention is to provide these inhibitors in purified forms to enable the determination of their amino acid sequence. A further object is to provide the amino acid sequences of certain IL-1 inhibitors. Furthermore, the identification of biologically-active analogs of such IL-1 inhibitors with enhanced or equivalent properties is also one of the objects of the invention.

Additionally, it is an object of this invention to provide a recombinant-DNA system for the production of the IL-1 inhibitors described herein. A further object cf the present invention includes providing purified forms of IL-1 inhibitors which would be valuable as pharmaceutical preparations exhibiting activity against IL-1.

Additional objects and advantages of the invention will be set forth in part in the description which follows, and in part will be obvious from the description or may be learned from the practice of the invention. The objects and advantages may be realized and attained by means of the instrumentalities and combinations particularly pointed out in the appended claims.

To achieve the objects and in accordance with the purposes of the present invention, IL-1 inhibitors are disclosed which exhibit inhibitory activity against IL-1. The preferred inhibitors have been isolated in a purified form from monocyte-conditioned medium with monocytes grown on IgG-coated plates.

Preferred inhibitors of the present invention are 1, 2 and 3. Inhibitors 1 and 2 are proteins running at positions characteristic of 22-23 kDa proteins on SDS-PAGE and eluting at 52 mM and 60 mM NaCl, respectively, from a Mono Q FPLC column under specified conditions. Inhibitor 3 is a protein running at a position characteristic of a 20 kD protein on SDS-PAGE and eluting at 48 mM NaCl from a Mono Q FPLC column under the specified conditions. Additionally, to achieve the objects and in accordance with the purposes of the present invention, pharmaceutical compositions containing, at least one of the active ingredients, an IL-1 inhibitor in accordance with the present invention or its biologically-active analog as set forth herein are disclosed.

Moreover, to achieve the objects and in accordance with the purposes of the present invention, a recombinant-DNA system for the creation of these IL-1 inhibitors and their analogs is also disclosed. A preferred embodiment of this system includes at least one cDNA clone or its synthetic equivalent encoding at least one IL-1 inhibitor along with vectors and cells constituting an expression system capable of expressing the IL-1 inhibitors disclosed herein. Antisera for use in identifying these cDNA clones is also provided. Expression systems for producing these IL-1 inhibitors using these cDNA clones, their analogs, or other DNA sequences encoding these inhibitors are also provided.

BRIEF DESCRIPTION OF THE FIGURES

FIGS. 1a and 1b depict the protein profile of the Mono Q chromatography of two metabolically-labelled monocyte supernatants. The cells were cultured on IgG (1a) or fetal calf serum (1b) coated plates.

FIG. 2b is an autoradiogram of the gels shown in FIG. 2a.

FIG. 3a presents chromatography data with the radioactivity pattern superimposed. FIG. 3b presents silver stained gels run on samples of the fractions indicated in FIG. 3a.

FIGS. 5a and b present Western analysis of mouse antisera.

FIGS. 8a and 8b present chromotography data. FIG. 8c presents a silver stained gel run on samples of fractions indicated in FIG. 8b. FIG. 8d presents an autoradiogram.

FIGS. 9a and 9b present data on IL-li-β. FIG. 9a presents chromotography data. FIG. 9b presents SDS-PAGE data.

FIG. 13 depicts a part of the DNA sequence of the protein coding region of lambda GT10-ILli-2A and the predicted amino acid sequence according to Example 6.

FIG. 14 depicts the nucleotide sequence of GT10-ilII-2A.

FIG. 15 depicts a peptide including, inter alia, an IL-li sequence and a secretory leader sequence.

DESCRIPTION OF THE PREFERRED EMBODIMENT

Figure 2A:
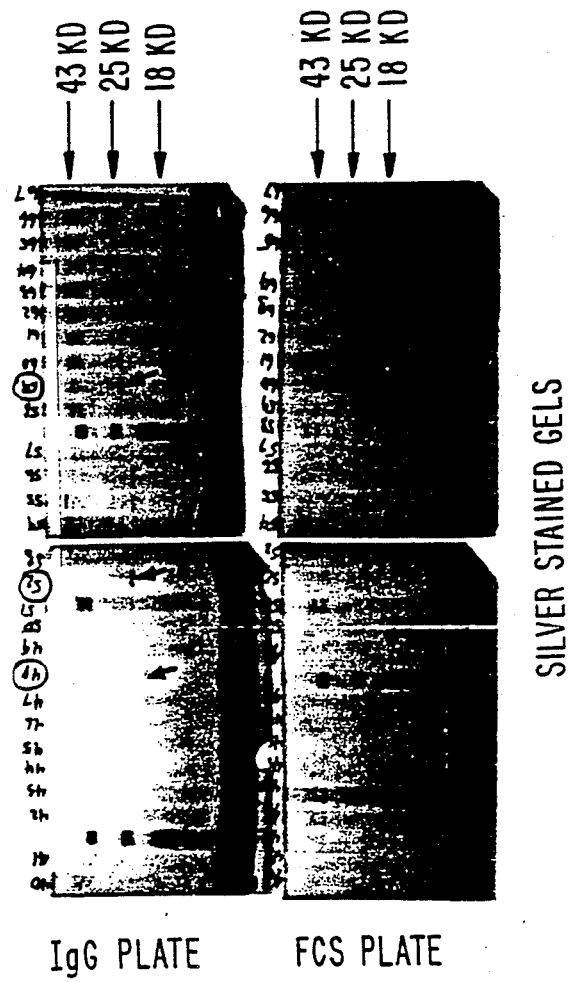
FIG. 2a shows silver stained gels of fractions from the regions indicated in FIGS. 1a and 1b.

Reference will now be made in detail to the presently preferred embodiments of the invention, which, together with the following examples, serve to explain the principles of the invention.

A. Inhibitor from Human Monocytes

As noted above, the present invention relates to IL-1 inhibitors which have been isolated in a purified form. Preferably, the IL-1 inhibitors of the present invention are derived from human monocyte conditioned medium where the monocytes are grown on IgG coated vessels. In addition, the invention encompasses substantially purified IL-1 inhibitors of any origin which are biologically equivalent to the inhibitor derived from human monocyte-contained medium.

By "biologically equivalent," as used throughout the specification and claims, we mean compositions of the present invention that are capable of preventing IL-1 action in a similar fashion, but not necessarily to the safe degree, as the native IL-1 inhibitor isolated from monocytes By "substantially homologous" as used throughout the ensuing specification and claims, is meant a degree of homology to the native IL-1 inhibitor isolated from monocyte-conditioned medium in excess of that displayed by any previously reported IL-1 inhibitors. Preferably, the degree of homology in excess of 70 percent, more preferably in excess of 80 percent and even more preferably in excess of 90 per cent. A particularly preferred group of inhibitors are in excess of 95 percent homologous with the native inhibitor. The percentage of homology as described is calculated as the percentage of amino acid residues found in the smaller of the two sequences that align with identical amino acid residues in the sequence being compared when four gaps in a length of 100 amino acids may be introduced to assist in that alignment as set forth by Dayhoff, M. D. in *Atlas of Protein Sequence and Structure* Vol.5, p. 124 (1972), National Biochemical Research Foundation, Washington, D.C., specifically incorporated herein by reference.

The preferred IL-1 inhibitors of the present invention have been derived from monocyte-conditioned medium and, for the first time, have been isolated in a purified form. For the purposes of the present application, "pure form" or "purified form" when used to refer to the IL-1 inhibitors disclosed herein, shall mean a preparation which is substantially free of other proteins which are not IL-1 inhibitor proteins. Preferably, the IL-1 inhibitors of the present invention are at least 90% pure and preferably 95% pure.

At least three purified IL-1 inhibitors have been isolated by the methods of the Example. These include inhibitor 1, inhibitor 2 and inhibitor 3. Inhibitor 1 is behaving as a 22–23 kDa molecule on SDS-PAGE with an approximate isoelectric point of 4.8 and eluting from a Mono Q FPLC column at around 52 mM NaCl in Tris buffer, pH 7.6. Inhibitor 2 is also a 22–23 kDa protein, pI=4.8, but eluting from a Mono Q column at 60 mM NaCl. Inhibitor 3 is a 20 kDa protein and elutes from a Mono Q column at 48 mM NaCl. Inhibitors 1, 2 and 3 are related immumologically and functionally. Having obtained these inhibitors in purified forms has enabled the present inventors to obtain their amino acid sequences. Using the purified inhibitors disclosed for the first time herein and methods such as those described in and by ABI Protein Sequencer technical manuals supplied with the ABI Protein Sequencer, a substantial proportion of the amino acid sequences of these inhibitors can be deduced.

Example 3 shows amino acid sequence data obtained of three species of IL-1 inhibitors, namely IL-$l_i$-X, IL-$l_i$-α and IL-$l_i$-β.

The present inventors have discovered at least one antibody raised against an IL-1 inhibitor. Other polyclonal and monoclonal antibodies against this and other IL-1 inhibitors may be prepared by methods known to those of ordinary skill in the art. One particular polyclonal antibody is described in Example 4.

B. Recombinant Inhibitor

1. General

A recombinant DNA method for the manufacture of an IL-1 inhibitor is now disclosed. In one embodiment of the invention, the active site functions in a manner biologically equivalent to that of the native IL-1 inhibitor isolated from human. A natural or synthetic DNA sequence may be used to direct production of the IL-1 inhibitors. This method comprises:

(a) Preparation of a DNA sequence capable of directing a host cell to produce a protein having IL-1 inhibitor activity;

(b) Cloning the DNA sequence into a vector capable of being transferred into and replicated in a host cell, such vector containing operational elements needed to express the DNA sequence;

(c) Transferring the vector containing the synthetic DNA sequence and operational elements into a host cell capable of expressing the DNA encoding IL-1 inhibitor;

(d) Culturing the host cells under conditions appropriate for amplification of the vector and expression of the inhibitor;

(e) Harvesting the inhibitor; and (f) Permitting the inhibitor to assume an active tertiary structure whereby it possesses IL-1 inhibitory activity.

2. DNA Sequences

DNA sequences contemplated for use in this method are discussed in part in Example 5 and in part in Example 6. It is contemplated that these sequences include synthetic and natural DNA sequences. The natural sequences further include cDNA or genomic DNA segments.

Example 6 provides a molecular clone of DNA encoding a protein identical to that isolated in Examples 1-3. In Example 6, a plaque, GT10-ILli-2A, was isolated from a GT10 Library. The phage within this plaque was propagated and the DNA was isolated and digested with EcoRI. An EcoRI fragment of 1850 base pairs carries the coding sequence for IL1 inhibitor. FIG. 13 shows the partial DNA sequence of the EcoRI fragment.

In light of the teachings contained herein and procedures known, other synthetic polynucleotide sequences will be available to one of ordinary skill in the art. As an example of the current state of the art relating to polynucleotide synthesis, one is directed to Matteucci, M. D. and Caruthers, M. H., in J. Am. Chem. Soc. 103:3185 (1981) and Beaucage, S. L. and Caruthers, M. H. in Tetrahedron Lett. 22:1859 (1981), and to the instructions supplied with an ABI oligonucleotide synthesizer, each of which is specifically incorporated herein by reference.

These synthetic sequences may be identical to the natural sequences described in more detail below or they may contain different nucleotides. In one embodiment, if the synthetic sequences contain nucleotides different from those found in the natural DNA sequences of this invention, it is contemplated that these different sequences will still encode a polypeptide which has the same primary structure as IL-li isolated from monocytes. In an alternate embodiment, the synthetic sequence containing different nucleotides will encode a polypeptide which has the same biological activity as the IL-li described herein.

Additionally, the DNA sequence may be a fragment of a natural sequence, i.e., a fragment of a polynucleotide which occurred in nature and which has been isolated and purified for the first time by the present inventors. In one embodiment, the DNA sequence is a restriction fragment isolated from a cDNA library.

In an alternative embodiment, the DNA sequence is isolated from a human genomic library. An example of such a library useful in this embodiment is set forth by Lawn et al. in Cell 15:1157-1174 (1978), specifically incorporated herein by reference.

In a preferred version of this embodiment, it is contemplated that the natural DNA sequence will be obtained by a method comprising:

(a) Preparation of a human cDNA library from cells, preferably monocytes, capable of generating an IL-1 inhibitor in a vector and cell capable of amplifying and expressing all or part of that cDNA;

(b) Probing the human DNA library with at least one probe capable of binding to the IL-1 inhibitor gene or its protein product;

(c) Identifying at least one clone containing the gene coding for the inhibitor by virtue of the ability of the clone to bind at least one probe for the gene or its protein product;

(d) Isolation of the gene or portion of the gene coding for the inhibitor from the clone or clones chosen;

(e) Linking the gene, or suitable fragments thereof, to operational elements necessary to maintain and express the gene in a host cell.

The natural DNA sequences useful in the foregoing process may also be identified and isolated through a method comprising:

(a) Preparation of a human genomic DNA library, preferably propagated in a recArecBC *E. coli* host;

(b) Probing the human genomic DNA library with at least one probe capable of binding to an IL-1 inhibitor gene or its protein product;

(c) Identification of at least one clone containing the gene coding for the inhibitor by virtue of the ability of the clone to bind at least one probe for the gene or its protein product;

(d) Isolation of the gene coding for the inhibitor from the clone(s) identified; and (e) Linking the gene, or suitable fragments thereof, to operational elements necessary to maintain and express the gene in a host cell.

In isolating a natural DNA sequence suitable for use in the above-method, it is preferred to identify the two restriction sites located within and closest to the end portions of the appropriate gene or sections of the gene. The DNA segment containing the appropriate gene is then removed from the remainder of the genomic material using appropriate restriction endonucleases. After excision, the 3' and 5' ends of the DNA sequence and any exxon junctions are reconstructed to provide appropriate DNA sequences capable of coding for the N- and C- termini of the IL-1 inhibitor protein and capable of fusing the DNA sequence to its operational elements.

3. Vectors (a) Microorganisms, especially *E. coli*

The vectors contemplated for use in the present invention include any vectors into which a DNA sequence as discussed above can be inserted, along with any preferred or required operational elements, and which vector can then be subsequently transferred into a host cell and replicated in such cell. Preferred vectors are those whose restriction sites have been well documented and which contain the operational elements preferred or required for transcription of the DNA sequence. However, certain embodiments of the present invention are also envisioned which employ currently undiscovered vectors which would contain one or more of the cDNA sequences described herein. In particular, it is preferred that all of these vectors have some or all of the following characteristics: (1) possess a minimal number of host-organism sequences; (2) be stably maintained and propagated in the desired host; (3) be capable of being present in a high copy number in the desired host; (4) possess a regulatable promoter positioned so as to promote transcription of the gene of interest; (5) have at least one marker DNA sequence coding for a selectable trait present on a portion of the plasmid separated from that where the DNA sequence will be inserted;

and (6) a DNA sequence capable of terminating transcription.

In various preferred embodiments, these cloning vectors containing and capable of expressing the DNA sequences of the present invention contain various operational elements. These "operational elements," as discussed herein, include at least one promoter, at least one Shine-Dalgarno sequence and initiator codon, and at least one terminator codon. Preferably, these "operational elements" also include at least one operator, at least one leader sequence for proteins to be expoited from intracellular space, at least one gene for a regulator protein, and any other DNA sequences necessary or preferred for appropriate transcription and subsequence translation of the vector DNA.

Certain of these operational elements may be present in each of the preferred vectors of the present invention It is contemplated that any additional operational elements which may be required may be added to these vectors using methods known to those of ordinary skill in the art, particularly in light of the teachings herein.

In practice, it is possible to construct each of these vectors in a way that allows them to be easily isolated, assembled and interchanged. This facilitates assembly of numerous functional genes from combinations of these elements and the coding region of the DNA sequences. Further, many of these elements will be applicable in more than one host. It is additionally contemplated that the vectors, in certain preferred embodiments, will contain DNA sequences capable of functioning as regulators ("operators"), and other DNA sequences capable of coding for regulator proteins.

(i) Regulators

These regulators, in one embodiment, will serve to prevent expression of the DNA sequence in the presence of certain environmental conditions and, in the presence of other environmental conditions, will allow transcription and subsequent expression of the protein coded for by the DNA sequence. In particular, it is preferred that regulatory segments be inserted into the vector such that expression of the DNA sequence will not occur, or will occur to a greatly reduced extent, in the absence of, for example, isopropylthio-beta-D-galactoside. In this situation, the transformed microorganisms containing the DNA sequence may be grown to at a desired density prior to initiation of the expression of IL-li. In this embodiment, expression of the desired protein is induced by addition of a substance to the microbial environment capable of causing expression of the DNA sequence after the desired density has been achieved.

(ii) Promoters

The expression vectors must contain promoters which can be used by the host organism for expression of its own proteins. While the lactose promoter system is commonly used, other microbial promoters have been isolated and characterized, enabling one skilled in the art to use them for expression of the recombinant IL-li.

(iii) Transcription Terminator

The transcription terminators contemplated herein serve to stabilize the vector. In particular, those sequences as described by Rosenberg, M. and Court, D., in Ann. Rev. Genet. 13:319-353 (1979), specifically incorporated herein by reference, are contemplated for use in the present invention.

(iv) Non-Translated Sequence

It is noted that, in the preferred embodiment, it may also be desirable to reconstruct the 3' or 5' end of the coding region to allow incorporation of 3' or 5' non-translated sequences into the gene transcript. Included among these non-translated sequences are those which stabilize the mDNA as they are identified by Schmeissner, U., McKenney, K., Rosenberg, M and Court, D. in J. Mol. Biol. 176:39-53 (1984), specifically incorporated herein by reference.

(v) Ribosome Binding Sites

The microbial expression of foreign proteins requires certain operational elements which include, but are not limited to, ribosome binding sites. A ribosome binding site is a sequence which a ribosome recognizes and binds to in the initiation of protein synthesis as set forth in Gold, L., et al., Ann. Rev. Microbio. 35:557-580; or Marquis, D. M., et al., Gene 42:175-183 (1986), both of which are specifically incorporated herein by reference. A preferred ribosome binding site is GAGGC-GCAAAAA(ATG).

(vi) Leader Sequence and Translational Coupler

Additionally, it is preferred that DNA coding for an appropriate secretory leader (signal) sequence be present at the 5' end of the DNA sequence as set forth by Watson, M. E. in Nucleic Acids Res. 12:5145-5163, specifically incorporated herein by reference, if the protein is to be excreted from the cytoplasm. The DNA for the leader be in a position which allows the production of a fusion protein in which the leader sequence is immediately adjacent to and covalently joined to the inhibitor, i.e., there must be no transcription or translation termination signals between the two DNA coding sequences. The presence of the leader sequence is desired in part for one or more of the following reasons. First, the presence of the leader sequence may facilitate host processing of the IL-li. In particular, the leader sequence may direct cleavage of the initial translation product by a leader peptidase to remove the leader sequence and leave a polypeptide with the amino acid sequence which has potential protein activity. Second, the presence of the leader sequence may facilitate purification of the IL-li, through directing the protein out of the cell cytoplasm. In some species of host microorganisms, the presence of an appropriate leader sequence will allow transport of the completed protein into the periplasmic space, as in the case of some E. coli. In the case of certain E. coli, Saccharomyces and strains of Bacillus and Pseudomonas, the appropriate leader sequence will allow transport of the protein through the cell membrane and into the extracellular medium. In this situation, the protein may be purified from extracellular protein. Thirdly, in the case of some of the proteins prepared by the present invention, the presence of the leader sequence may be necessary to locate the completed protein in an environment where it may fold to assume its active structure, which structure possesses the appropriate protein activity.

In one preferred embodiment of the present invention, an additional DNA sequence is located immediately preceding the DNA sequence which codes for the IL-1 inhibitor. The additional DNA sequence is capable of functioning as a translational coupler, i.e., it is a DNA sequence that encodes an RNA which serves to position ribosomes immediately adjacent to the ribosome binding site of the inhibitor RNA with which it is contiguous. In one embodiment of the present invention, the translational coupler may be derived using the DNA sequence

TAACGAGGCGCAAAAAAT-
GAAAAAGACAGCTATCGCGATCTT-
GGAGGATGATTAAATG and methods currently known to those of ordinary skill in the art related to translational couplers.

(vii) Translation Terminator

The translation terminators contemplated herein serve to stop the translation of mRNA. They may be either natural, as described by Kohli, J., Mol. Gen. Genet. 182:430-439; or synthesized, as described by Pettersson, R. F. Gene 24:15-27 (1983), both of which references are specifically incorporated herein by reference.

(viii) Selectable Marker

Additionally, it is preferred that the cloning vector contain a selectable marker, such as a drug resistance marker or other marker which causes expression of a selectable trait by the host microorganism. In one embodiment of the present invention, the gene for ampicillin resistance is included in the vector while, in other plasmids, the gene for tetracycline resistance or the gene for chloramphenicol resistance is included.

Such a drug resistance or other selectable marker is intended in part to facilitate in the selection of transformants. Additionally, the presence of such a selectable marker in the cloning vector may be of use in keeping contaminating microorganisms from multiplying in the culture medium. In this embodiment, a pure culture of the transformed host microorganisms would be obtained by culturing the microorganisms under conditions which require the induced phenotype for survival.

The operational elements as discussed herein are routinely selected by those of ordinary skill in the ar in light of prior literature and the teachings contained herein. General examples of these operational elements are set forth in B. Lewin, Genes, Wiley & Sons, New York (1983), which is specifically incorporated herein by reference Various examples of suitable operational elements may be found on the vectors discussed above and may be elucidated through review of the publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth by Maniatis et al. in Molecular Cloning, Cold Spring Harbor Laboratories (1984), which is specifically incorporated herein by reference.

In construction of the cloning vectors of the present invention, it should additionally be noted that multiple copies of the DNA sequence and its attendant operational elements may be inserted into each vector. In such an embodiment, the host organism would produce greater amounts per vector of the desired IL-1 inhibitor. The number of multiple copies of the DNA sequence which may be inserted into the vector is limited only by the ability of the resultant vector, due to its size, to be transferred into and replicated and transcribed in an appropriate host cell.

(b) Other Microorganisms

Vectors suitable for use in microorganisms other than E. coli are also contemplated for this invention. Such vectors are described in Table 1. In addition, certain preferred vectors are discussed below.

TABLE 1

| HOSTS | REGULATED PROMOTERS | INDUCER | TRANSCRIPTION TERMINATOR | MRNA STABILIZATION | TRANSCRIPTIONAL START SITE & LEADER PEPTIDE | MARKER | RS BINDING SITE |
|---|---|---|---|---|---|---|---|
| E. coli | Lac[1], Tac[2] Lambda pL Trp[5] | IPTG increased temperature IAA addition or tryptophan depletion | rrnB[6] rrnC[7] | ompA[8] lambda int[9] trp[10] | bla[11] ompA[12] phoS | ampicillin[14] tetracycline[14, 15] chloramphenical[16] | |
| Bacillus | *alpha amylase[17] *subtilisin[18] *p-43[19] spac-I[26] | IPTG | E. coli rrn rrn BT.T[20] | | B. amy neutral protease[21] B. amy alpha-amylase[22] B. subt. subtilisin[23] | Kan[r 24] Cam[r 25] | B. amy neural protease B. amy alpha-amylase[22] |
| Pseudomonas | Trp[27] (E. coli) Lac (E. coli) Tac (E. coli) | IAA addition, or tryptophan depletion IPTG | | | phospholipase C[28] exotoxin A[29] | sulfonamide[30] streptomycin[30] | Trp (E. coli) |
| Yeast | Gal 1[31], 10[32] Adh 1[33], II[34] Pho 5 | Glucose depletion and galactose Glucose depletion Phosphate | Cyc 1 Una Alpha factor Sac 2 | | Invertase[36] Acid phosphatase[36] Alpha Factor | Ura 3[37] Leu 2[38] His 3 Tap 1 | |

TABLE 1-continued

| HOSTS | REGULATED PROMOTERS | INDUCER | TRANS-CRIPTION TER-MINATOR | MRNA STABILIZATION | TRANSCRIPTIONAL START SITE & LEADER PEPTIDE | MARKER | RS BINDING SITE |
|---|---|---|---|---|---|---|---|
| | | depletion | | | | | |

*non-regulated
[1]Backman, K., Ptashne, M. and Gilbert, W. Proc. Natl. Acad. Sci. USA 73, 4174–4178 (1976).
[2]de Boer, H. A., Comstock, L. J., and Vasser, M. Proc. Natl. Acad. Sci. USA 80, 21–25 (1983).
[3]Shimatake, H. and Rosenberg, M. Nature 292, 128–132 (1981).
[4]Derom, C., Gheysen, D. and Fiers, W. Gene 17, 45–51 (1982).
[5]Hallewell, R. A. and Emtage, S. Gene 9, 27–47 (1986).
[6]Brosius, J., Dull, T. J., Sleeter, D. D. and Noller, H. F. J. Mol. Biol. 148, 107–127 (1981).
[7]Normanly, J., Ogden, R. C., Horvath, S. J. and Abelson, J. Nature 321, 213–219 (1986).
[8]Belasco, J. G., Nilsson, G., von Gabain, A. and Cohen, S. N. Cell 46, 245–251 (1986).
[9]Schmeissner, U., McKenney, K., Rosenberg M. and Court. D. J. Mol. Biol. 176, 39–53 (1984).
[10]Mott, J. E., Galloway, J. L. and Platt, T. EMBO J. 4, 1887–1891 (1985).
[11]Koshland, D. and Botstein, D. Cell 20, 749–760 (1980).
[12]Movva, N. R., Nakamura, K. and Inouye, M. J. Mol. Biol. 143, 317–328 (1980).
[13]Surin, B. P., Jans, D. A., Fimmel, A. L., Shaw, D. C., Cox, G. B. and Rosenberg, H. J. Bacteriol. 157, 772–778 (1984).
[14]Sutcliffe, J. G. Proc. Natl. Acad. Sci. USA 75, 3737–3741 (1908).
[15]Peden, K. W. C. Gene 22, 277–280 (1983).
[16]Alton, N. K. and Vapnek, D. Nature 282, 864–869 (1979).
[17]Yang, M., Galizzi, A., and Henner, D. Nuc. Acids Res. 11(2), 237–248 (1983).
[18]Wong, S.-L., Price, C. W., Goldfarb, D. S., and Doi, R. H. Proc. Natl. Acad. Sci. USA 81, 1184–1188 (1984).
[19]Wang, P.-Z., and Doi, R. H. J. Biol. Chem. 259, 8619–8625, (1984).
[20]Lin, C.-K., Quinn, L. A. Rodriquez, R. L. J. Cell Biochem. Suppl. (9B), p. 198 (1985).
[21]Vasantha, N., Thompson, L. D., Rhodes, C., Banner, C., Nagle, J., and Filpula, D. J. Bact. 159(3), 811–819 (1984).
[22]Palva, I., Sarvas, M., Lehtovaara, P., Sibazkov, M., and Kaariainen, L. Proc. Natl. Acad. Sci. USA 79, 5582–5586 (1982).
[23]Wong, S.-L., Pricee, C. W., Goldfarb, D. S., and Doi, R. H. Proc. Natl. Acad. Sci. USA 81, 1184–1188 (1984).
[24]Sullivan, M. A., Yasbin, R. E., and Young, F. E. Gene 29, 21–46 (1984).
[25]Vasantha, N., Thompson, L. D., Rhodes, C., Banner, C. Nagle, J., and Filpula, D. J. Bact. 159(3), 811–819 (1984).
[26]Yansura, D. G. and Henner, D. J. PNAS 81, 439–443 (1984).
[27]Gray, G. L., McKeown, K. A., Jones, A. J. S., Seeburg, P. H. and Heyneker, H. L. Biotechnology, 161–165 (1984).
[28]Lory, S., and Tai, P. C. Gene 22, 95–101 (1983).
[29]Liu, P. V. J. Infect. Dis. 130 (suppl), 594–599 (1974).
[30]Wood, D. G., Hollinger, M. F., and Tindol, M. B. J. Bact. 145, 1448–1451 (1981).
[31]St. John, T. P. and Davis, R. W. J. Mol. Biol. 152, 285–315 (1981).
[32]Hopper, J. E., and Rowe, L. B. J. Biol. Chem. 253, 7566–7569 (1978).
[33]Denis, C. L., Ferguson, J. and Young, E. T. J. Biol. Chem. 258, 1165–1171 (1983).
[34]Lutsdorf, L. and Megnet, R. Archs. Biochem. Biophys. 126, 933–944 (1968).
[35]Meyhack, B., Bajwa, N., Rudolph, H. and Hinnen, A. EMBO. J. 6, 675–680 (1982).
[36]Watson, M. E. E. Nucleic Acid Research 12, 5145–5164 (1984).
[37]Gerband, C. and Guerineau, M. Curr. Genet. 1, 219–228 (1980).
[38]Hinnen, A., Hicks, J. B. and Fink, G. R. Proc. Natl. Acad. Sci. USA 75, 1929–1933 (1978).
[39]Jabbar, M. A., Sivasubramanian, N. and Nayak, D. P. Proc. Natl. Acad. Sci. USA 82, 2019–2023 (1985).

(i) Pseudomonas Vectors

Several vector plasmids which autonomously replicate in a broad range of Gram negative bacteria are preferred for use as cloning vehicles in hosts of the genus Pseudomonas. Certain of these are described by Tait, R. C., Close, T. J., Lundquist, R. C., Hagiya, M., Rodriguez, R. L., and Kado, C. I. In Biotechnology, May, 1983, pp. 269–275; Panopoulos, N. J. in *Genetic Engineering in the Plant Sciences*, Praeger Publishers, New York, N.Y., pp. 163–185 (1981); and Sakagucki, K. in Current Topic in Microbiology and Immunology 96:31–45 (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in *Plasmids of Medical, Environmental and Commercial Importance*, Timmis, K. N. and Puhler, A. eds., Elsevier/North Holland Biomedical Press (1979), specifically incorporated herein by reference. The advantages of RSF1010 are that it is relatively a small, high copy number plasmid which is readily transformed into and stably maintained in both *E. coli* and Pseudomonas species. In this system, it would be preferred to use the Tac expression system as described for Escherichia, since it appears that the *E. coli* trp promoter is readily recognized by Pseudomonas RNA polymerase as set forth by Sakagucki, K. in Current Topics in Microbiology and Immunology 96:31–45 (1982) and Gray, G. L., MCKeown, K. A., Jones, A. J. S., Seeburg, P. H., and Heyneker, H. L. in Biotechnology, Feb. 1984, pp. 161–165, both of which are specifically incorporated herein by reference. Transcriptional activity may be further maximized by requiring the exchange of the promoter with, e.g., an *E. coli* or P. aeruginosa trp promoter. Additionally, the lacI gene of *E. coli* would also be included in the plasmid to effect regulation.

Translation may be coupled to translation initiation for any of the Pseudomonas proteins, as well as to initiation sites for any of the highly expressed proteins of the type chosen to cause intracellular expression of the inhibitor.

In those cases where restriction minus strains of a host Pseudomonas species are not available, transformation efficiency with plasmid constructs isolated from *E. coli* are poor. Therefore, passage of the Pseudomonas cloning vector through an r−m+strain of another species prior to transformation of the desired host, as set forth in Bagdasarian, M., et al., *Plasmids of Medical, Environmental and Commercial Importance*, pp. 411–422, Timmis and Puhler eds., Elsevier/North Holland Biomedical Press (1979), specifically incorporated herein by reference, is desired.

(ii) Bacillus Vectors

Furthermore, a preferred expression system in hosts of the genus Bacillus involves using plasmid pUB110 as the cloning vehicle. As in other host vectors system, it is possible in Bacillus to express the IL-li of the present invention as either an intracellular or a secreted protein.

The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering*, Vol. 2, Setlow and Hollander eds., Plenum Press, New York, N.Y., pp. 115-131 (1980), specifically incorporated herein by reference. For the expression and secretion of the IL-li from *B. subtilis*, the signal sequence of alpha-amylase is preferably coupled to the coding region for the protein. For synthesis of intracellular inhibitor, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilli*, Ganesan, A. T. and Hoch, J. A., eds., Academic Press, pp. 249-263 (1984), specifically incorporated by reference. The lacI gene of *E. coli* would also be included in the plasmid to effect regulation.

(iii) Clostridium Vectors

One preferred construction for expression in Clostridium is in plasmid pJU12, described by Squires, C. H. et al., in J. Bacteriol. 159:465-471 (1984) and specifically incorporated herein by reference, transformed into *C. perfringens* by the method of Heefner, D. L. et al., as described in J. Bacteriol. 159:460–464 (1984), specifically incorporated herein by reference. Transcription is directed by the promoter of the tetracycline resistance gene. Translation is coupled to the Shine-Dalgarno sequences of this same $tet^r$ gene in a manner strictly analogous to the procedures outlined above for vectors suitable for use in other hosts.

(iv) Yeast Vectors

Maintenance of foreign DNA introduced into yeast can be effected in several ways as described by Botstein, D. and Davis, R. W., in *The Molecular Biology of the Yeast Saccharomyces*, Cold Spring Harbor Laboratory, Strathern, Jones and Broach, eds., pp. 607–636 (1982), specifically incorporated hereby by reference. One preferred expression system for use with host organisms of the genus Saccharomyces harbors the IL-li gene on the 2 micron plasmid. The advantages of the 2 micron circle include relatively high copy number and stability when introduced into cir° strains. These vectors preferably incorporate the replication origin and at least one antibiotic resistance marker from pBR322 to allow replication and selection in *E. coli*. In addition, the plasmid will preferably have the two micron sequence and the yeast LEU2 gene to serve the same purposes in LEU2 defective mutants of yeast.

If it is contemplated that the recombinant IL-1 inhibitors will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of the IL-1 inhibitor.

(c) Mammalian Cells

The cDNA for the IL-1 inhibitor will serve as the gene for expression of the inhibitor in mammalian cells. It should have a sequence that will be efficient at binding ribsomes such as that described by [Kozak, in Nucleic Acids Research 15:8125–8132 (1987), specifically incorporated herein by reference,] and should have coding capacity for a leader sequence (see section 3(a)(vi)) to direct the mature protein out of the cell in a processed form. The DNA restriction fragment carrying the complete cDNA sequence can be inserted into an expression vector which has a transcriptional promoter and a transcriptional enhancer as described by Guarente, L. in Cell 52:303–305 (1988) and Kadonaga, J. T. et al., in Cell 51:1079–1090 (1987), both of which are specifically incorporated herein by reference. The promoter may be regulatable as in the plasmid pMSG (Pharmacia Cat. No. 27450601) if constitutive expression of the inhibitor is harmful to cell growth. The vector should have a complete polyadenylation signal as described by Ausubel, F. M. et al. in Current Protocols in Molecular Biology, Wiley (1987), specifically incorporated herein by reference, so that the mRNA transcribed from this vector is processed properly. Finally, the vector will have the replication origin and at least one antibiotic resistance marker from pBR322 to allow replication and selection in *E. coli*.

In order to select a stable cell line that produces the IL-1 inhibitor, the expression vector can carry the gene for a selectable marker such as a drug resistance marker or carry a complementary gene for a deficient cell line, such as a dihydrofolate reductase (dhfr) gene for transforming a $dhfr^-$ cell line as described by Ausubel et al., supra. Alternatively, a separate plasmid carrying the selectable marker can be cotransformed along with the expression vector.

4. Host Cells/Transformation

The vector thus obtained is transferred into an appropriate host cell. These host cells may be microorganisms or mammalian cells.

(a) Microorganisms

It is believed that any microorganism having the ability to take up exogenous DNA and express those genes and attendant operational elements may be chosen After a host organism has been chosen, the vector is transferred into the host organism using methods generally known to those of ordinary skill in the art. Examples of such methods may be found in Advanced Bacterial Genetics by R. W. Davis et al.. Cold Spring Harbor Press, Cold Spring Harbor, N.Y. (1980). which is specifically incorporated herein by reference. It is preferred, in one embodiment, that the transformation occur at low temperatures, as temperature regulation is contemplated as a means of regulating gene expression through the use of operational elements as set forth above In another embodiment, if osmolar regulators have been inserted into the vector, regulation of the salt concentrations during the transformation would be required to insure appropriate control of the foreign genes.

It is preferred that the host microorganism be a facultative anaerobe or an aerobe. Particular hosts which may be preferable for use in this method include yeasts and bacteria. Specific yeasts include those of the genus Saccharomyces, and especially *Saccharomyces cerevisiae* Specific bacteria include those of the genera *Bacillus, Escherichia*, and *Pseudomonas*, especially *Bacillus subtilis* and *Escherichia coli*. Additional host cells are listed in Table I, supra.

(b) Mammalian Cells

The vector can be introduced into mammalian cells in culture by several techniques such as calcium phosphate:DNA coprecipitation, electroporation, or protoplast fusion. The preferred method is coprecipitation with calcium phosphate as described by Ausubel et al., supra.

Many stable cell types exist that are transformable and capable of transcribing and translating the cDNA sequence, processing the precursor IL-li and secreting the mature protein. However, cell types may be variable with regard to glycosylation of secreted proteins and post-translational modification of amino acid residues, if any. Thus, the ideal cell types are those that produce a recombinant IL-1 inhibitor identical to the natural molecule.

5. Culturing Engineered Cells

The host cells are cultured under conditions appropriate for the expression of the IL-1 inhibitor These conditions are generally specific for the host cell, and are readily determined by one of ordinary skill in the art in light of the published literature regarding the growth conditions for such cells and the teachings contained herein For example, Bergey's Manual of Determinative Bacteriology, 8th Ed., Williams & Wilkins Company, Baltimore, Md., which is specifically incorporated herein by reference, contains information on conditions for culturing bacteria. Similar information on culturing yeast and mammalian cells may be obtained from Pollack, R. Mammalian Cell Culture, Cold Spring Habor Laboratories (1975), specifically incorporated herein by reference.

Any conditions necessary for the regulation of the expression of the DNA sequence, dependent upon any operational elements inserted into or present in the vector, would be in effect at the transformation and culturing stages. In one embodiment, cells are grown to a high density in the presence of appropriate regulatory conditions which inhibit the expression o( the DNA sequence. When optimal cell density is approached, the environmental conditions are altered to those appropriate for expression of the DNA sequence. It is thus contemplated that the production of the IL-1 inhibitor will occur in a time span subsequent to the growth of the host cells to near optimal density, and that the resultant IL-1 inhibitor will be harvested at some time after the regulatory conditions necessary for its expression were induced.

6. Purification (a) IL-li Produced From Microorganisms

In a preferred embodiment of the present invention, the recombinant IL-1 inhibitor is purified subsequent to harvesting and prior to assumption of its active structure. This embodiment is preferred as the inventors believe that recovery of a high yield of re-folded protein is facilitated if the protein is first purified. However, in one preferred, alternate embodiment, the IL-1 inhibitor may be allowed re-fold to assume its active structure prior to purification. In yet another preferred., alternate embodiment, the IL-1 inhibitor is present in its re folded, active state upon recovery from the culturing medium.

In certain circumstances, the IL-1 inhibitor will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein. If the IL-1 inhibitor does not assume its proper, active structure, any disulfide bonds which have formed and/or any noncovalent interactions which have occurred will first be disrupted by denaturing and reducing agents, for example, guanidinium chloride and beta-mercaptoethanol, before the IL-1 inhibitor is allowed to assume its active structure following dilution and oxidation of these agents under controlled conditions.

For purification prior to and after refolding, some combination of the following steps is preferably used: anion exchange chromatography (MonoQ or DEAE-Sepharose), gel filtration chromatography (superose), chromatofocusing (MonoP), and hydrophobic interaction chromatography (octyl or phenyl sepharose). Of particular value will be antibody affinity chromatography using the IL-li-specific monoclonal antibodies (described in Example 3).

(b) IL-li Produced from Mammalian Cells

IL-li produced from mammalian cells will be purified from conditioned medium by steps that will include ion exchange chromatography and immunoaffinity chromatography using monoclonal antibodies described in Example 3. It will be apparent to those skilled in the art that various modifications and variations can be made in the processes and products of the present invention. Thus, it is intended that the present invention cover the modifications and variations of this invention provided they come within the scope of the appended claims and their equivalents.

It is to be understood that application of the teachings of the present invention to a specific problem or environment will be within the capabilities of one having ordinary skill in the art in light of the teachings contained herein. Examples of the products of the present invention and representative processes for their isolation and manufacture appear in the following.

The following examples illustrate various presently preferred embodiments of the present invention. The publications provided in this examples are specifically incorporated by reference herein.

EXAMPLES

Example 1

Protein Preparation

A. Materials

Hank's Balanced Salt Solution (HBSS) and RPMI were purchased from Mediatech, Washington, D.C. Lymphoprep was obtained from Accurate Chemical and Scientific Corp., Westbury, N.Y. Human IgG, MTT, rabbit anti-prostaglandin $E_2$ antiserum, ammonium bicarbonate, dithiothreitol, complete and incomplete Freund's adjuvants, hypoxanthine, aminopterin, and thymidine were purchased from Sigma Chemical Co., St. Louis, Missouri. C3H/HeJ mice were purchased from Jackson Labs, Bar Harbor, Me. BALB/c mice and P3 myeloma cells were obtained from Drs. John Kappler and Philippa Marrack at the National Jewish Center for Immunology and Respiratory Medicine (NJC/IRM), Denver, Colo. Recombinant human IL-1 was obtained from Cistron Biotechnology, Pine Brook, N.J purified phytohemagglutinin was purchased from Wellcome Diagnostics, Research Triangle Park, N.C. Human foreskin fibroblasts from primary cultures were obtained from Dr. Richard Clark at the NJC/IRM, Denver, Colorado. Monoclonal mouse anti-rabbitt IgG antibodies were purchased from AIA reagents, Aurora, Colo. Low methionine RPMI was made using a Select-Amine kit from GIBCO Laboratories, Grand Island, N.Y. [$^{35}$S]-methionine, diphenyloxazole, and [$^{14}$C]-iodoacetic acid were obtained from DuPont NEN, Chicago, Ill. Fetal calf serum was purchased from HyClone Laboratories, Logan, Utah. Mono Q and Superose 12 columns were purchased from Pharmacia, Inc., Piscataway, N.J. C4-reversed phase columns were obtained from Synchrom, Inc., Lafayette, Ind. C8-reversed phase columns were obtained from Applied Biosystems, Inc., Foster City, Calif. Acetonitrile and polyethylene glycol 8000 were purchased from J. T. Baker Chemical Co., Phillipsburg, N.J. Trifluroacetic acid and guanidine hydrochloride were obtained from Pierce Chemicals, Rockford, Ill. Endoproteinase Lys C was obtained from Boehringer Mannheim Biochemicals, Indianapolis, Ind. The microtitering plates used for PGE2 ELISA were Nunc-Immuno Plate I obtained from Intermountain Scientific Corporation, Bountiful, Utah. The plates used for hybridoma production were from Costar, Cambridge, Mass.

B. Generation of Monocyte IL-1 Inhibitor

Human leukocytes were obtained from normal donors by leukophoresis, resuspended in Hank's balanced salt solution (HBAA) at 1 part packed cells to 1 part HBSS, underlayed with Lymphoprep and spun at 400 xg for 30' at room temperature. The mononuclear fraction was taken (typically $4-\times 10^9$ cells were obtained per donor), washed in HBSS without $Ca^{++}$ or $Mg^{++}$, suspended in serum-free RPMI and plated on petri dishes coated with normal human IgG made LPS free by chromatography over Sephapex G200 ($6\times 10^7$ cells in 10 ml per 100 mm dish). All reagents contained less than 10 pg/ml LPS. The cells were cultured 24-48 hr, and the resulting conditioned medium constituted the crude IL-1 inhibitor (IL-li) supernatant. Typically, the cells from one donor yielded 700-900 ml crude IL-li supernatant.

C. Assays for the IL-1 Inhibitor

Two IL-1 assays have been used routinely to detect the IL-li. Thymocytes ($1\times 10^6$ cells from 4 to 6 week old C3H/HeJ mice) respond to 1.0 unit/ml of recombinant human IL-1 plus 1 ug/ml phytohaemaglutinin by proliferatirg half-maximally, as measured by 3H-thymidine incorporation or uptake of the tetrazolium salt MTT (Mosmann, T., J. Immunol Method, 65:55-61 (1983)) after three days of stimulation. Crude IL-li supernatant fully inhibits this proliferative response at a 1/13 dilution. Human dermal fibroblasts ($1\times 10^5$ cells per well in a 96 well plate) typically respond to 0.5 units/ml recombinant human IL-1 by secreting, at 6 hours of stimulation, approximately 50,000 pg/ml PGE2 that can be measured by ELISA. This assay is as sensitive to IL-li as is the thymocyte assay.

D. Metabolic Labeling of the IL-1 Inhibitor

The IL-li was metabolically labeled by culturing mononuclear leukocytes for 48 hours on IgG-coated plates (as described in B) in serum-free RPMI containing only 0.75 ug/ml cold methionine (15 ug/ml is normal) and to which was added 0.5 mCi $^{35}$S-methionine (1151 Ci/mmol) per $10^7$ cells. Control labelings were performed serum rather than IgG. Assays on such control supernatants showed that very little IL-li was secreted when the cells were cultured on on fetal calf serum-coated plates.

E. Purification of the IL-1 Inhibitor Protein

Figure 2B:
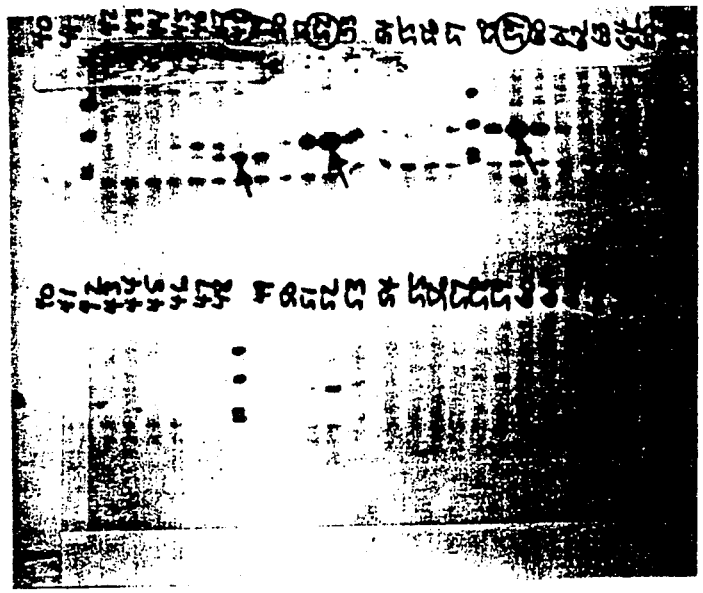

Crude IL-li supernatants were made 1.0 M in sodium chloride, incubated on ice for 1 hour and centrifuged at 10,000 rpm for 15 minutes. The supernatants, which contained all of the inhibitor activity but only 20% of the initial protein, were then dialyzed extensively at 4° C. versus 0.025 M Tris, pH 7.6 containing 0.1% sucrose (the A buffer) for gradient fractionation of proteins on a Mono Q anion exchange column. Following dialysis the inhibitor-containing solutions were recentrifuged at 10,000 rpm for 15 minutes and then passed through 0.22 u nylon filters. The supernatants were typically combined with 10 ml of similarly prepared supernatant from a metabolic labeling and loaded onto Mono Q-Superose (Pharmacia FPLC) columns with bed volumes of either 1.0 ml or 8.0 ml, washed with A buffer until the OD280 of the effluent returned to baseline, and carefully chromatographed using a linear sodium chloride gradient (0.025 M to 0.10 M) in buffer A. Column fractions were collected and analyzed for radioactivity and bioactivity. Samples of each fraction were also run on reduced 12.5% SDS-PAGE, silver stained, permeated with diphenyloxazole, dried and put onto film to obtain autoradiographic data. FIG. 1a shows the protein profile of the Mono Q chromatography of 40 ml crude Il-li supernatant mixed with 3 ml of metabolically labeled IL-li supernatant. Superimposed are the amount of radioactivity found in 50 ul of each fraction as well as the IL-li bioactivity as measured in the PGE2-production assay. Two major and one minor radioactive species are shown that perfectly correlate with three peaks of bioactivity. FIG. 1b shows the similar chromatography of 15 ml of crude Il-li supernatant mixed with 3 ml of supernatant from monocytes metabolically labeled on plates coated with fetal calf serum (FCS) rather than IgG. The levels of the three radioactive species discussed above are markedly diminished. FIG. 2a shows silver stained gels run on the fractions from the regions of interest in the chromatographies shown in FIGS. 1a and 1b. Note that the fractions of peak radioactivity and bioactivity in FIG. 1a (fractions 52 and 59) both show a major band at 22 Kd (marked with arrows) on SDS-PAGE. The third species (fraction 48 in FIG. 1a) shows a band at 20 kD on SDS-PAGE. Gel filtration experiments on crude IL-li have shown that the active molecule has a molecular weight of 18-25 Kd FIG. 2b is an autoradiogram of the gels shown in FIG. 2a. It can be readily seen that the protein bands at 20 and 22 Kd are the major radioactive species in those fractions.

Summarizing these results, we have shown that the metabolic labeling of monocytes plated on petri dishes coated with IgG results in radioactive species that are only poorly produced if the cells are plated on dishes coated with FCS. These induced radioactive species perfectly co-chromatograph with several species of IL-li bioactivity on Mono Q, and gels and resulting autoradiograms show that the three major induced molecules are proteins of the predicted molecular weight for IL-li.

Figure 3A:
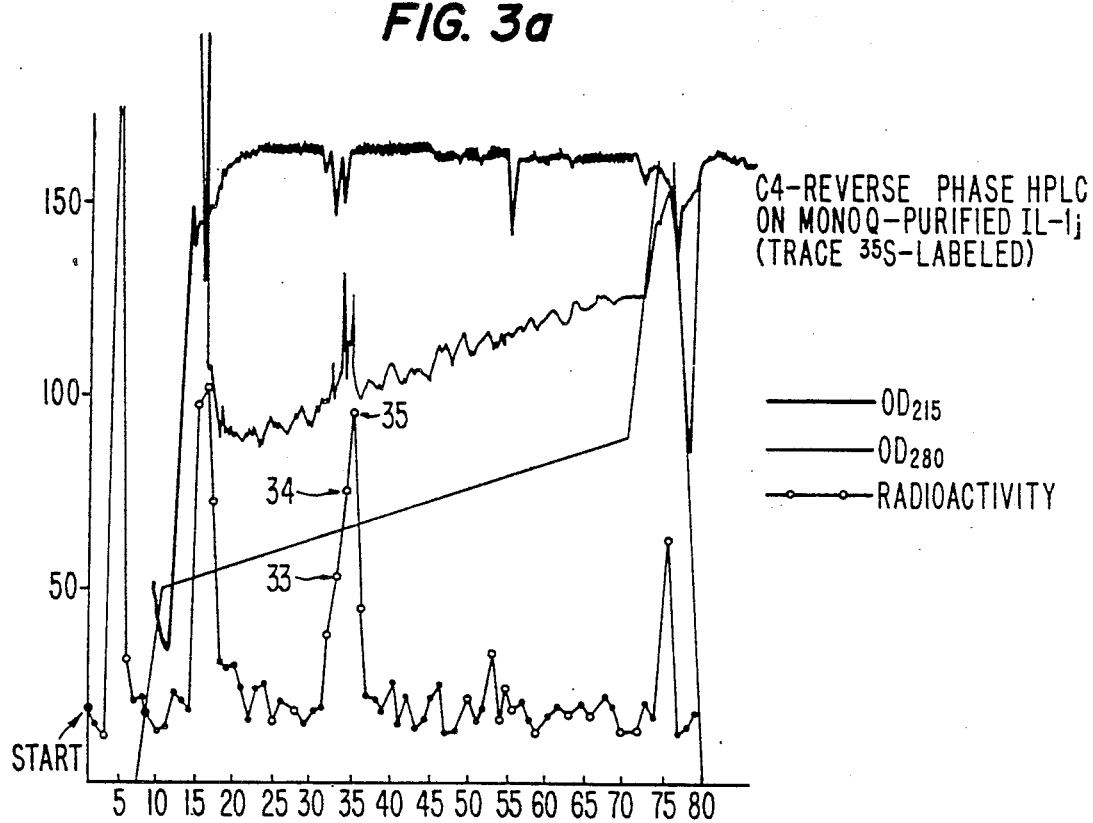
FIGS. 3a, b and c present data on the purified IL-li of Example 1.
Figure 3B:
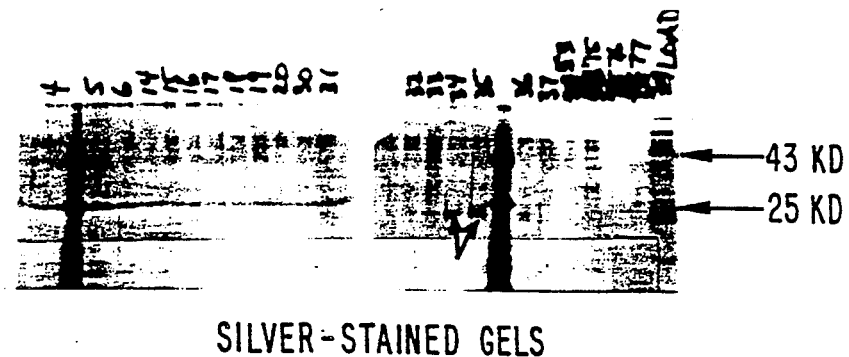
Figure 3C:
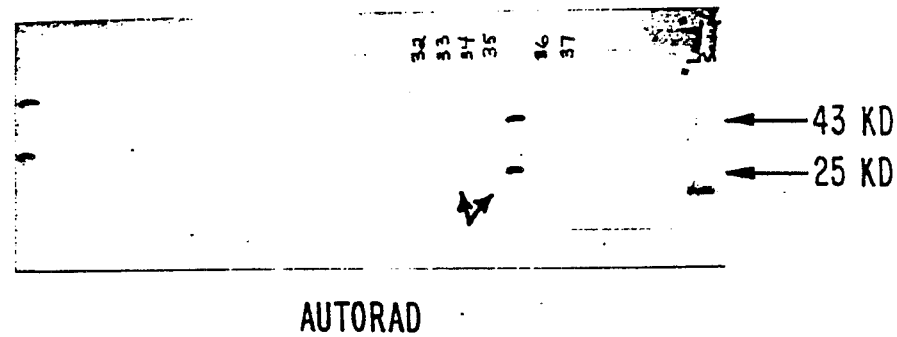
FIG. 3c presents autoradiograms of the gels in FIG. 3b.
Figure 4A:
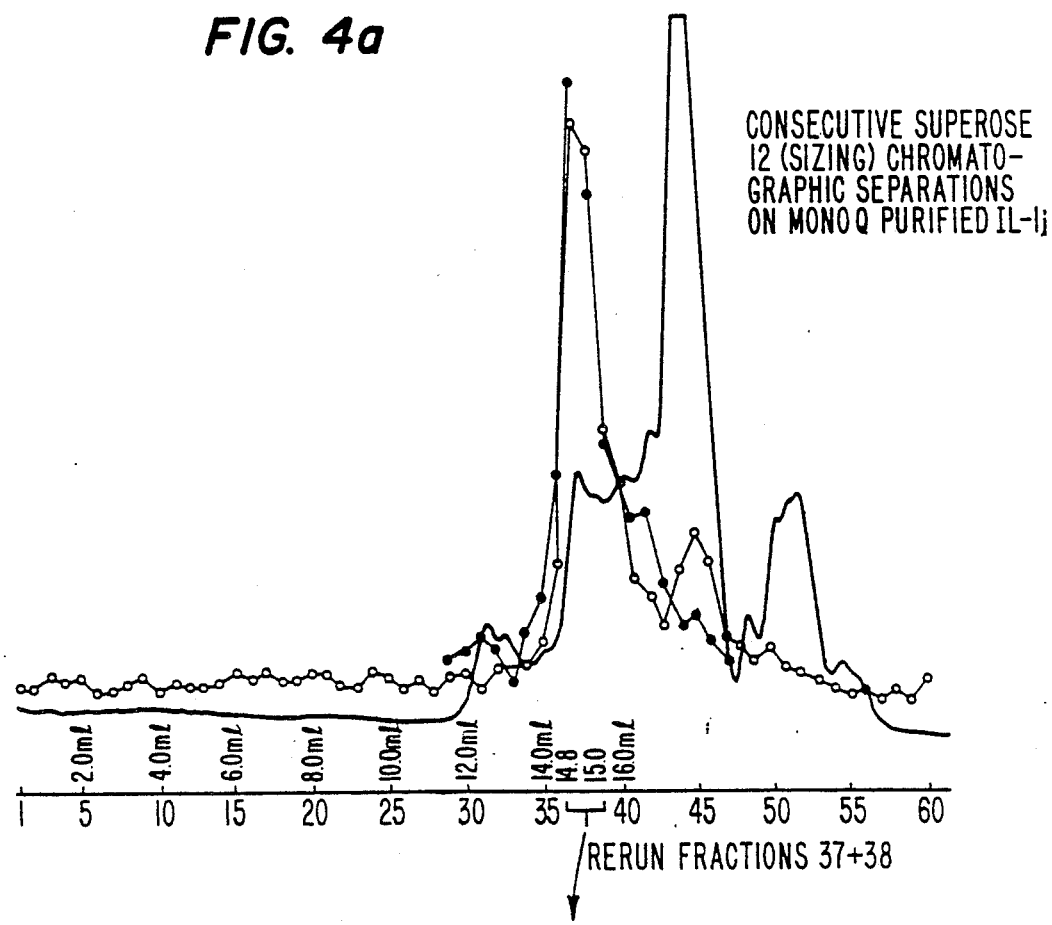
FIGS. 4a and b present the results of gel filtration chromatograms of Mono Q-purified IL-li.
Figure 4B:
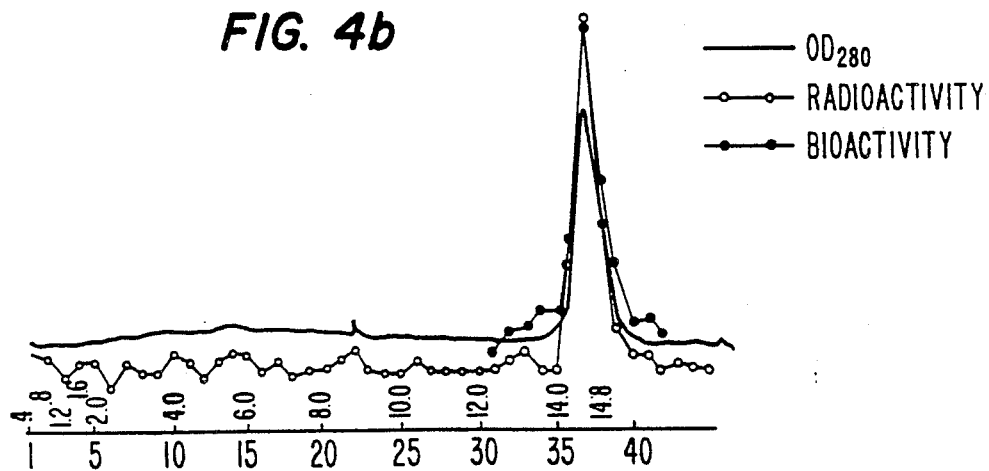

The IL-li molecules were further purified for sequencing in two ways First, Mono Q fractions with peak bioactivity and radioactivity were loaded onto a C4-reversed phase column and eluted with an H₂O/0.1% TFA acetonitrile/0.1% TFA gradient Since the IL-li molecule was trace labeled, samples from each fraction were directly counted for radioactivity and were also analyzed by SDS-PAGE followed by autoradiography. FIG. 3a shows such a chromatograph with the radioactivity pattern superimposed. The silver stained gels run on samples from each fraction (FIG. 3b) and subsequent autoradiograms of the gels (FIG. 3c) shows that the IL-li molecule is found in fractions 32–36. These fractions were dried down and sequenced Alternatively, the peak Mono Q fractions were dried by Speed Vac, resuspended in 0.4 ml 0.05 M NH₄HCO₃ and directly chromatographed two times on a 10×300 mm Superose 12 gel filtration column (Pharmacia FPLC) equilibrated in the same buffer, as shown in FIGS. 4a and 4b. Fractions were collected and samples of each were tested for radioactivity and bioactivity and were analyzed by silver stained and autoradiographed SDS-PAGE Appropriate fractions were then dried on a speed vac and sequenced.

Example 2

Proposed Sequencing of the IL-1 Inhibitor

Prior to sequencing, samples were dissolved in 6 M guanidine-HCl, pH 8.6, reduced for 4 hours at 37° C. under N₂ with 100-fold molar excess dithiothreitol over protein, and alkylated for 1 hour with 400-fold excess 14C-iodcacetic acid. In that case, the reactions would be desalted on a C8-reversed phase column, eluted, and partially dried. N-terminal sequences will be determined using an Applied Biosystems Protein Sequencer. To obtain internal sequences, samples which may have been reduced and alkylated would be digested with cyanogen bromide or proteolytic enzymes using methods known to those of ordinary skill in the art. Reactions will be dried, dissolved in 0.1% TFA/H₂O, and peptides will be separated using a C8-reverse phase column.

Example 3

Purification and Sequencing of the Species of IL-1 Inhibitors

A. IL-li-X, IL-li-a and IL li-h Species

The Mono Q purification of IL-li resolves the biological activity into three major species, as shown in FIG. 1a and described in Example 1, where the peak fractions for this activity are 48, 52, and 59 SDS-PAGE on samples of these fractions, as shown in FIG. 2a, reveal pertinent species at 20 kD, 22 kD, and 22 kD, respectively. Western analysis of such gels, using the mouse antisera discussed in Example 4 below, stains all three of these species. When IL-li is prepared from cells metabolically labeled with ³⁵S-methionine, during growth on plates coated with IgG, each of these bands is radioactive (as shown in FIG. 2b, the autoradiogram of the above-mentioned gel). Based on the logic discussed in Example 1, namely that parallel cells incubated in a non-inducing condition do not produce the IL-li bioactivity and do not produce these radioactive bands, we can conclude that these three species account for the biological activity. We have tentative-y named these species IL-li-X, IL-li-a, and IL-li-b, respectively.

B Purification and Sequencing of IL-li-X

Mono Q fractions containing IL-li-X and/or IL-li-a were further purified by reversed-phase HPLC chromatography on a Synchropak RP-4 (C4) column, and radioactive species were submitted for sequence analysis. Numerous attempts at directly sequencing RP-HPLC-purified IL-li-a and IL-li-b have failed, suggesting that they are chemically blocked at their N-termini However, one preparation of IL-li-a (IL-li-aB2p42) yielded the following sequence:

```
     1     5         10        15        20
     R P S G R K S S K M Q A F _ I S D V N Q
``` and subsequent preparations of IL-li-X, similarly purified by C4 RP-HPLC, have produced the same sequence:

```
              1         5         10'        15        20
PrepKxF24     _ _ _ _ _ _ _ _ _ M Q A F _ I D _ V N _ K _ F
and
PrepKxF23     R P _ _ R K _ L K M Q A F _ I
```

These are obviously part of the sequence found in the initial attempt at sequencing IL-li-a. It is the inventors' conclusion that the sequence data shown is the N-terminus of the 20 kD species called IL-li-X.

In these and all subsequent sequences an underlined position indicates either an inability to identify a residue or that ambiguity exists with respect to the residue identified. When two or more residues are put in one position, it indicates that more than one amino acid was detected at that sequencing step, and the more likely correct residue is on top.

C. Generation, Purification, and Sequencing of peptides of IL-li-a and IL-li-b

Figure 8A:
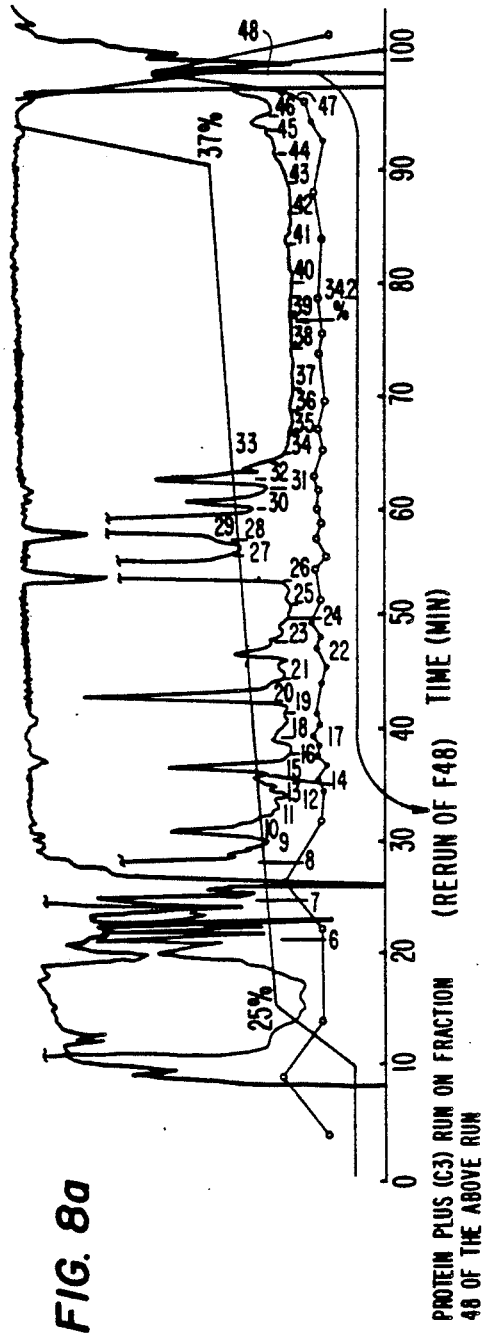
FIGS. 8a–d present data on IL-li-α.
Figure 8B:
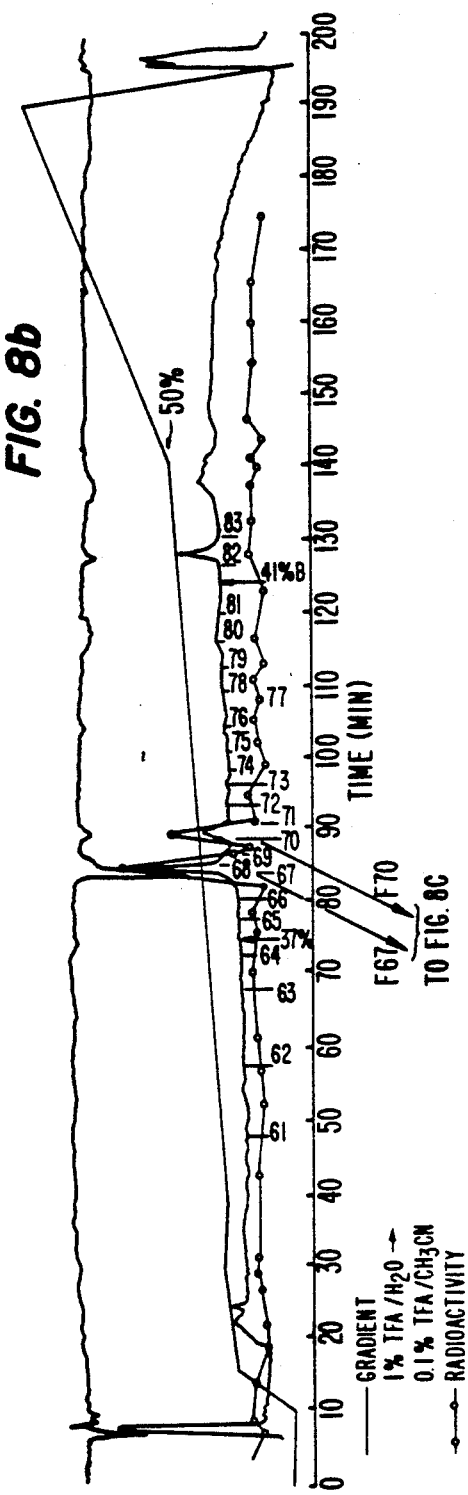
Figure 8C:
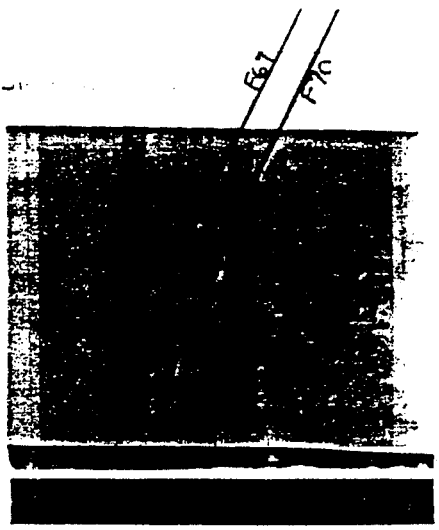
Figure 8D:
Figure 9B:
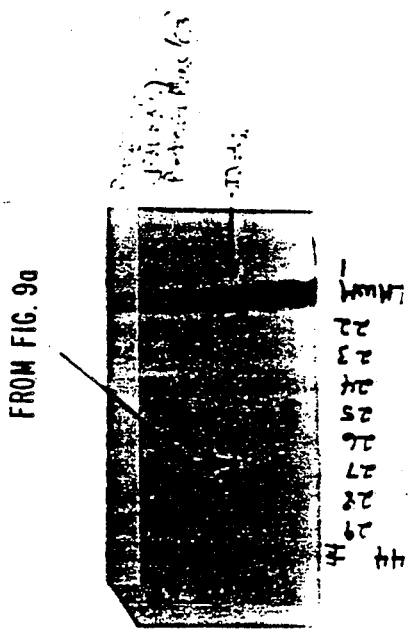

Since IL-li-a and IL-li-b are apparently chemically blocked at their N-termini, peptides of each were generated by endoproteinase digestion Specifically, Mono Q fractions containing either IL-li-a or IL-li-b were passed through a 4.6×250 C3-RPHPLC column (Zorbax Protein Plus., an acceptable alternative to the C-4 columns used in all previous experiments. Very gradual gradients (0.2% acetonitrile per minute at 0.5 ml/min) resolved the IL-li-a (FIG. 8a,b) or IL-li-b (FIG. 9a) away from the major contaminating radioactive species, human lysozyme. The identities of the purified species were confirmed by the presence of a single, radioactive, 22 kD protein on SDS-pAGE and subsequent autoradiograms (FIGS. 8c,d and 9b). The proteins were hand-collected into siliconized glass tubes and to each was added 25 ml of a 0.2% Tween-20 solution. The IL-li-containing fractions were then reduced in volume on a Speed-Vac to 50 ml, brought up to 300 ml by the addition of 1% NH₄HCO₃, followed by the addition of 1 mg of endoproteinase. In the case of IL-li-a, the enzyme used was Endoproteinase Lys C (Boehringer-Mannheim), while IL-li-b was cleaved with Endoproteinase Asp N (Boehringer-Mannheim). Cleavage was carried out at 37° C. for 16 hr, and then the volume of the reaction mix was reduced to 50 ml on a Speed Vac.

Figure 10:
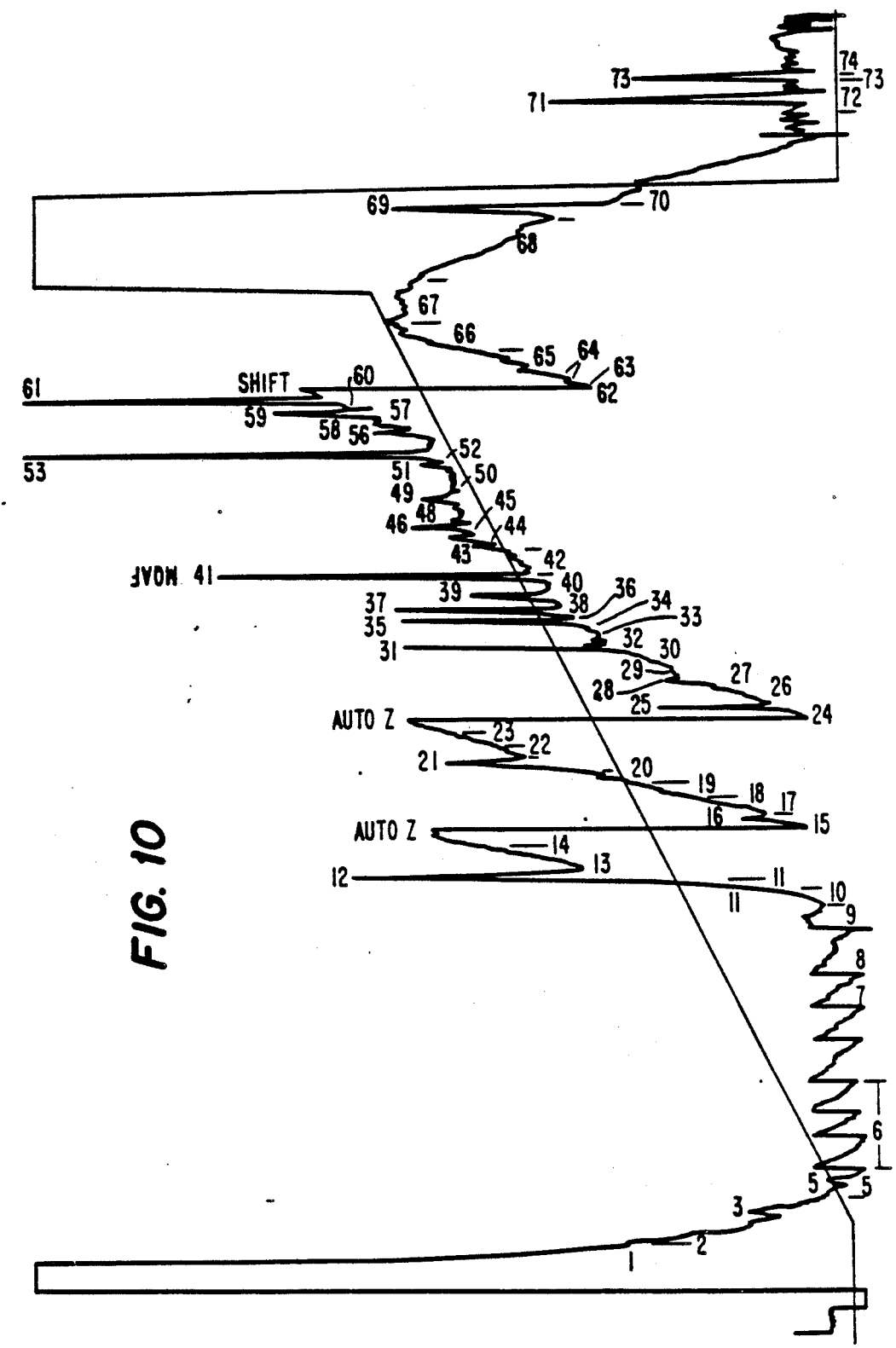
FIG. 10 presents data of IL-li-α peptide separation.
Figure 11:
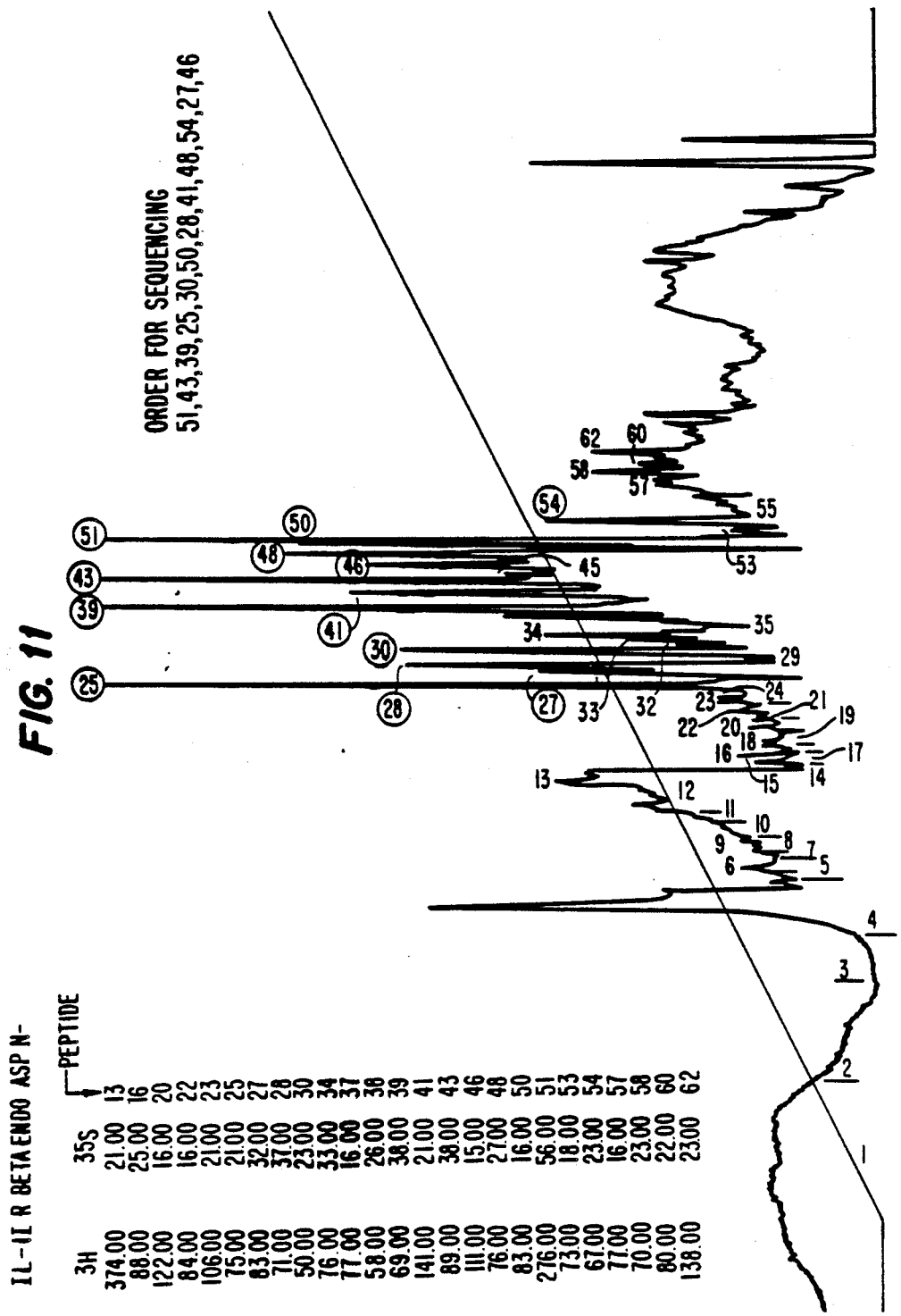
FIG. 11 presents data of IL-li-β peptide separation.

In the case of IL-li-a, the sample was directly chromatographed, whereas the IL-li-b sample was first reduced by the addition of 5 ml of 50 mM dithiothreitol in 2 M Tris, pH 8.0, reacted for 30 min at 37° C., and then carboxymethylated by addition of 1.1 umole $^3$H-iodoacetic acid in 10 ml ethanol (reacted 30 min at 37° C. in the dark) Separation of the peptides was performed on a 2.1×250 mm Brownlee Aquapore RP-300 (C8) narrow-bore column at a flow rate of 100 ml/min using a Beckman HPLC outfitted with microbore hardware and microbore-compatible pumps A 200 min 0–100% linear gradient was used (H$_2$O/0.1% TFA to acetonitrile/0.1% TFA). The peptide separations are shown in FIGS. 10 and 11. The sequence information obtained is as follows:

```
                    1         5              10
RaLysC-41          M  Q  A  F  _  I  _  D  V  N  Q  K 1         5              10              15              20         K  25                    P
RaLysC-53          _  F  Y  L  _  N  N  Q  L  V  A  _  Y  L  Q  G  P  N  V  N  L  E  E  Q  I  D  N  _  N 1         5 I            Y
RaLysC-61          _  F  A  T  T  R  H  V  H 1         5
RaLysC-31          F  Y  F  Q  E  D 1         5              10  V         15      N  20
                          G  E                    S     I  T        S
RaLysC-37          _  Q  D  F  T  _  L  Q  L  E  A  N  R  Q  S  Q  L  G  E  Q 1              5              10              15              20
RaLysC-35          _  _  _  E  T  R  L  Q  L  E  A  V  _  I  T  D  L  L  E  N 5              10              15         G   20         25
                    1      Q  K  T  F     L
RβAspN-51          D  V  N  P  I  E  P  Y  A  R  N  N  Q  L  V  A  S  Y  L  Q  G  P  N  V  N  L 1         5              10
RβAspN-43          D  E  G  V  M  V  T  K  F  Y  F  Q 1         5        K  10                15
RβAspN-39          _  P  S  G  R  K  S  S  F  M  Q  A  F  R  T  Q 1         5
RβAspN-25          D  K  R  F  A  F  I  R

1     I    5              10
                       S     L              Q
RβAspN-30          D  _  E  V  N  H  L  K  K  I  S
```

Two of the peptide sequences are obviously related to that which was obtained earlier from IL-li-X. One of these, RaLysC-41, is an IL-li-a sequence, and the other, RbAspN-51, is an IL-li-b sequence, arguing that the three species of Il-li are at least closely related proteins if not chemically and/or physically modified forms of a single original IL-li molecule. If the listed sequences are combined, the following composite sequences result:

```
                           |---------RaLysC-41------|    |-----------------------RaLysC-53----------------------|
|-----------RβAspN-39----------|  |-----------------------RβAspN-51-----------------------|
|----------------IL-1αβ2p42---------------|
                                                                                       G           K           P
R P S G R K S S K M Q A F R I S D V N Q K T F Y L R N N Q L V A S Y L Q G P N V L E E Q I D _ _ N

|---RaLysC-31---|
            |---------RβAspN-43---------|
            D E G V M V T K F Y F Q E D

|-----------------RaLysC-35,37----------------|
                                          N
                                          S
              G                    I           G      G
            M Q D E T R L Q L E A V R Q T D L L E N
```

```
|----RαLysC-61----|
|----RβAspN-25--|
                Y
D K R F A F I R H V H
                _ _
```

These composite sequences appear to be present in no other known polypeptides listed in the most recently updated Protein Identification Resource Database (PIR 16.0). The inventors believe that these sequences, or minor variants thereof, represent a class of molecules that are capable of acting as IL-1 inhibitors.

Example 4

Preparation of Antibodies Specific For the IL-1 Inhibitor

Ten week old BALB/c mice were injected subcutaneously with IL-li that was partially purified (400-fold) from crude supernatants by Mono Q-chromatography, dialyzed versus PBS, and emulsified with Complete Freund's Adjuvant. Each mouse received the IL-li purified from 5 ml of crude supernatant. The mice were boosted every two weeks with an equivalent amount of IL-li emulsifed with Incomplete Freund's Adjuvant, and serum samples were taken from the tails seven days after each boost. Antisera were tested for anti-IL-li activity by Western analysis of transblots of the immunogen run on SDS-PAGE, as shown in FIG. 5a. FIG. 5b shows that all of the mice were making anti-IL-li antibodies after three injections of IL-li.

Since monoclonal antibodies will be of great value in cloning the IL-li gene from an expression library, purifying the recombinant IL-li protein, and studying the biology of the molecule, we have begun the process of making a battery of monoclonal antibodies specific for Il-li. To produce B cell hybridomas, the above mice were injected intravenously with the same amount of IL-li in saline 24 hours prior to removal of the spleens. Splenocytes were teased out of the spleens into cold balanced salt solution (BSS), washed two times with BSS, mixed with P3 myeloma cells at a ratio of $2 \times 10^7$ P3 cells per $10^8$ splenic B cells and spun down. The cells were fused by the dropwise addition of 1 ml of warm, gassed (5% $CO_2$) PEG 6000 (40% polyethylene glycol 6000:60% minimal essential medium) to the dry pellet. Fused cells were washed with BSS and resuspended in 10 ml of rich media (10% FBS) containing $2 \times 10^5$ peritoneal cells per ml and the pellet was gently broken up using a 10 ml pipet. The volume was adjusted to 20 ml with the addition of more peritoneal cells in media, and the cells were plated out in 96 well plates at 0.1 ml/well. Plates were placed in a gas incubater and treated in the following manner thereafter:

Day 1—Add $3 \times$ HAT (hypoxanthine, aminopterin, thymidine) in rich medium to a final concentration of $1 \times$ Day 5—Change medium, replacing with 200 ul $1 \times$ HAT in rich medium Day 10—Begin checking for hybrid growth. Change medium, replacing with 200 ul $1 \times$ HAT in rich medium containing $1.5 \times 10^6$ peritoneal cells per ml.

When hybrid cells are nearly confluent in a well the supernatants are transferred for testing, and the cells are gently scraped with a pipet tip and transferred to 1 ml culture wells containing $1 \times$ HAT in rich medium plus $3 \times 10^6$ peritoneal cells per ml.

The supernatants from the confluent wells are tested for anti-IL-li activity using an ELISA in which partially purified IL-li (Mono Q-purified material identical to that injected into the mice) is bound to microtitering wells. Normal mouse sera and hyperimmune antisera are used as the negative and positive controls, respectively. Positive supernatants will be retested by ELISA on plates coated with homogeneously purified IL-li and by immunoprecipitation of purified metabolically labeled IL-li. Positive cells will then be cloned by limiting dilution and injected into pristane-treated mice for the generation of ascites. Large quantities of IL-li-specific antibodies can be produced by tissue culture or by massive generation and collection of ascitic fluid in mice. Purification of these antibodies and attachment thereof to insoluble beads will produce affinity adsorbents for the purification of the recombinant IL-li protein.

Example 5

Cloning the Il-li cDNA

It was shown that monocytes plated on IgG-coated petri dishes and cultured for 24 hours in the presence of [$^{35}$S]-methionine produced [$^{35}$S]-IL-li which could be identified by its chromotographic properties on Mono Q.

In order to determine when (during the 24 hour period) IL-li was being produced at a maximal rate, plated monocytes were exposed to [$^{35}$S]-methionine (pulsed) for a short, two-hour period, at which time a large excess of unlabelled methionine was added and incubated for an additional two hours. The medium was then collected and analyzed for ratiolabelled IL-li. This procedure was applied to monocytes at various times after plating of IgG-coated plates and it was found that exposing monocytes to [$^{35}$S]-methionine at 15 hours after plating produced the maximal amount of [$^{35}$S]-IL-li, indicating that IL-li mRNA in monocytes was at its maximal level 15 hours after plating on IgG.

Fresh monocytes were then plated on LPS free IgG obtained as in Example 1B. After incubating in RPMI media for 15 hours at 37° C., the cells are washed with phosphate buffered saline then lysed with 4M guanidinium thiocyanate; 25 mM sodium citrate, pH 7, 0.5% sarcosyl, 0.1 M 2-mercaptoethanol. Total RNA was then isolated from this lysate by the AGPC method of P. Chomczynski and N. Sacchi described in Analytical Biochemistry, vol. 162, pp. 156–159 (1987).

Poly A+ RNA was isolated by oligo dT cellulose chromatography by the method of Aviv, H. and Leder, P. (1972) Proc. Natl. Acad. Sci. (USA) 69:1408–1412 precipitated with ethanol and dissolved to a concentration of 0.36 ug/ul. One microgram to poly A+ RNA was used to prepare cDNA according to Gubler, U. and Hoffman, B. J. (1983) Gene 25:263–169.

The cDNA was incorporated into a lambda gtll expression library using Eco Rl linkers from Boehringer Mannheim catalog No. 988448 or New England Bio Lab No. 1070 and instructions provided by these manufacturers.

The resulting library, which contains $10^6$ independent clones, was screened on *E. coli* Y1090 rk− (Promega Biotec) with an appropriate polyclonal antibody to IL-li as described previously using screening conditions described by R. A. Young and R. W. Davis [(1983) PNAS 80:1194–1198]. Positive signals will be detected using a biotinylated second antibody (such as goat anti-mouse IgG, Bethesda Research Labs) followed by a strepavidin-alkaline phosphatase conjugate (Bethesda Research Labs), as described by Bayer, E. A. and Wilchek, M. (1979) in Methods in Biochemical Analysis, and Guesdon, J. L. Ternynch, T. and Avrameas, S. (1979) J. Histochem. Cytochem 27:1131–1138 and according to manufacturer's instructions.

Example 6

Preparation and Sequencing of Gene Encoding Il-li cDNA prepared as described in Example 5 was incorporated into the cloning vector lambda GT10. This cDNA was first methylated using EcoRI methylase with S-adenosyl-methionine as the substrate, EcoRI linkers were attached in a ligation reaction, and excess linkers were removed by digestion with EcoRI endonuclease and chromatography on a CL6B spin column A ligation reaction containing 0.124 ug of linkered, size-selected cDNA and 1 ug of EcoRI-cut and phosphatase treated lambda GT10 was performed, and the products of this ligation reaction were packaged using GIGA-PACK GOLD packaging extracts (Stratagene). This yielded a library of $1 \times 10^7$ members.

In order to screen this GT10 library, oligonucleotde (antisense) probes were synthesized based on protein and peptide sequence presented in Example 3. The sequences of the probes and of their corresponding peptide sequence are as follows.

with EcoRI, divided into five equal aliquots, and electrophoresed on a 1% agarose gel.

Figure 12A:
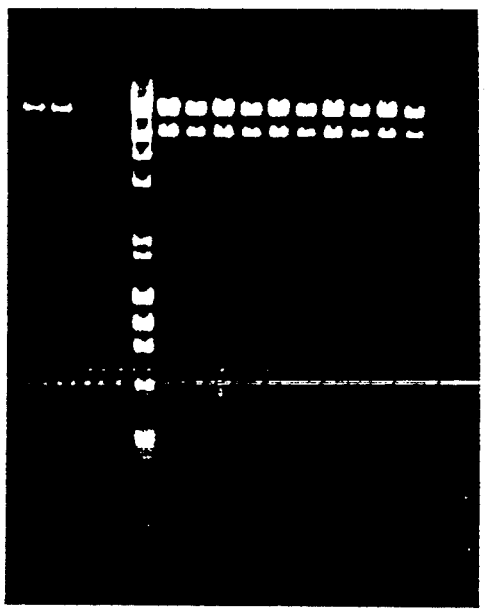
FIG. 12A is a photograph of the gel with the GT10-ILli-2A digested with EcoRI after electrophoresis according to Example 6.

After electrophoresis, this gel was stained with ethidium bromide. A photograph of this gel is shown in FIG. 12 A. Lanes 6, 8, 10, 12, and 14 contain the five aliquots from the EcoRI digestion. Lane 5 contains a mixture of wild-type lambda DNA cut with HindIII and ØX174 RF DNA cut with HaeIII (New England Biolabs) which are useful as molecular weight markers. FIG. 12a shows that GT10-ILli-2A contains an EcoRI fragment that is 1850 base pairs in length.

In order to demonstrate more conclusively that this 1850 bp fragment carries coding sequence for the IL1 inhibitor, a Southern blot was performed as follows. The DNA fragments in the gel shown in FIG. 12A were blotted onto nitrocellulose using standard methods The nitrocellulose was then cut lengthwise into five strips such that each strip contained the DNA from lanes 6, 8, 10, 12, and 14. The strips were then individually hybridized to each of the five oligonucleotide probes (above) which were labeled at the 5' end with $^{32}$P phosphate. The oligonucleotide concentration was 1 pmole/ml and the hybridization temperatures were as follows.

| LANE | PROBE | TEMPERATURE |
|------|-------|-------------|
| 6 | #ILlil-3 | 35° C. |
| 8 | #ILlil-4 | 42° C. |
| 10 | #ILlil-5 | 42° C. |
| 12 | #ILlil-6 | 40° C. |
| 14 | #ILlil-7 | 35° C. |

Figure 12B:
FIG. 12B presents data of an autoradiogram of a Southern blot of the gel shown in FIG. 12A.

After washing, the strips were lined up and taped together to reform the original nitrocellulose sheet. This was autoradiographed in the presence of an intensifying screen at −70° C. for 24 hours. FIG. 12B is a photograph of this autoradiograph. It provides evi- Probe #ILlil-3    T T $^T_C$ T A C G T $^T_C$ C G N A A $^A_G$ 5'
                   Lys  Met  Gln  Ala  Phe Probe #ILlil-4    T T $^T_C$ A A $^A_G$ A T $^A_G$ A A $^A_G$ G T $^T_C$ C T $^T_C$ C T 5'
                   Lys  Phe  Tyr  Phe  Gln  Glu  Asp Probe #ILlil-5    T A C C A N T G N T T $^T_C$ A A $^A_G$ A T $^A_G$ A A 5'
                   Met  Val  Thr  Lys  Phe  Tyr  Phe Probe #ILlil-6    C T $^A_G$ C A N T T $^A_G$ G T $^T_C$ T T $^T_C$ T G 5'
                   Asp  Val  Asn  Gln  Lys  Thr Probe #ILlil-7    T T $^A_G$ G T $^T_C$ T T $^T_C$ T G N A A $^A_G$ A T 5'
                   Asn  Gln  Lys  Thr  Phe  Tyr Note:
N = A, G, C, and T Probe #ILlil-3 was $^{32}$P-phosphorylated at its 5' end and used to screen $3 \times 10^5$ plaques of the library. The probe hybridized reproducibly to three plaques, and out of these, one plaque was shown to also hybridize to probe #ILlil-4. This plaque, GT10-ILli-2A, was cultivated and the DNA was isolated using Lambdasorb (Promega) according to the manufacturer's instructions. GT10-ILli-2A has been deposited at American Type Culture Collection (ATCC) in Rockville, Md. under Accession No. 40488 The DNA was digested dence that all of the probes hybridize specifically to the 1850 bp fragment, proving that this fragment carries substantial coding sequences for the IL1 inhibitor.

In order to determine its DNA sequence, GT10-ILII-2A DNA was digested with EcoRI, electrophoresed on a 1% agarose gel, and the 1850 bp fragment was isolated. This fragment was ligated with EcoRI-digested M13 mp19 and transformed into *E. coli* strain JM109. Transformants were screened by looking for those lacking beta-galactosidase activity. Five such transformants were isolated, single-stranded DNA was prepared, and sequencing was performed according to Sanger et al. The DNA sequence of three of the transformants corresponded to the 3' end of the mRNA, while two transformants provided protein coding sequence. In FIG. 13, the DNA sequence is shown that was obtained for the protein coding region of the cDNA.

FIG. 13 also shows the predicted amino acid sequence. The amino acid sequence from the first amino acid Alanine to the 29th amino acid Proline and from the 79th amino acid isoleucine to the end is the hypothesized amino acid sequence. The predicted amino acid sequence from the 30th amino acid Proline to the 78th amino acid Proline agrees with the peptide sequences described in Example 3.

Example 7

Sequencing GT10-IL-lI-2A and IL-li

A portion of GT10-ILlI-2A has been sequenced and is set forth in FIG. 14. The DNA encodes a protein containing amino acid sequences that are characteristic of IL-li (nucleotides 99–557). However, it is believed that several modifications may be made to this protein before it is secreted into the extracellular milieu. These modifications may or may not be essential for the protein to have activity as an IL-li.

GT10-ILli-2A encodes at least 32 amino acids N-terminal (nucleotides 3–98) to the amino terminus of the form of IL-li known as X. It is believed that included in these 32 amino acids is a secretory leader sequence that starts at the M encoded by nucleotides 24–26, directs the nascent IL-li to the extracellular milieu, and is then removed by a leader peptidase, and possibly other peptidases. The extent to which this sequence is removed in forms alpha and beta of IL-li is presently unknown, but the N-terminus of these forms is thought to be close to that of form X. Removal of the secretory leader sequence is probably required for the protein to have effective IL-li activity.

Nucleotides 349–351 of GT10-ILlI-2A encode an N residue that is part of a concensus N-glycosylation site. On the basis of their susceptibility to digestion with N-glycanase it is believed that forms alpha and beta of IL-li are glycosylated. Since form X is not believed to be susceptible to digestion with this enzyme it is believed that it is not glycosylated, although this remains a possibility that could easily be demonstrated by one of ordinary skill in the art of protein sequencing using the information provided here It is believed that glycosylation at this N residue is not required for the protein to show effective IL-li activity.

Nucleotides 99–101 of GT10-ILli-2A encode a P (see FIG. 15), but no P has been detected at this position (the N-terminus) of form X of IL-li. It is possible that this residue has been modified in the mature protein. It is believed that modification of this residue is not essential for effective IL-li activity.

The presently unknown N-terminus residues of forms alpha and beta are not wholly detectable by Edman degradation and are likely to be modified following removal of some of the N-terminal residues of the protein encoded by GT10-ILli-2A. It is believed that is modification is not essential for effective IL-li activity.

EXAMPLE 8

Expression of Genes Encoding IL-li in Animal Cells

Figure 6:
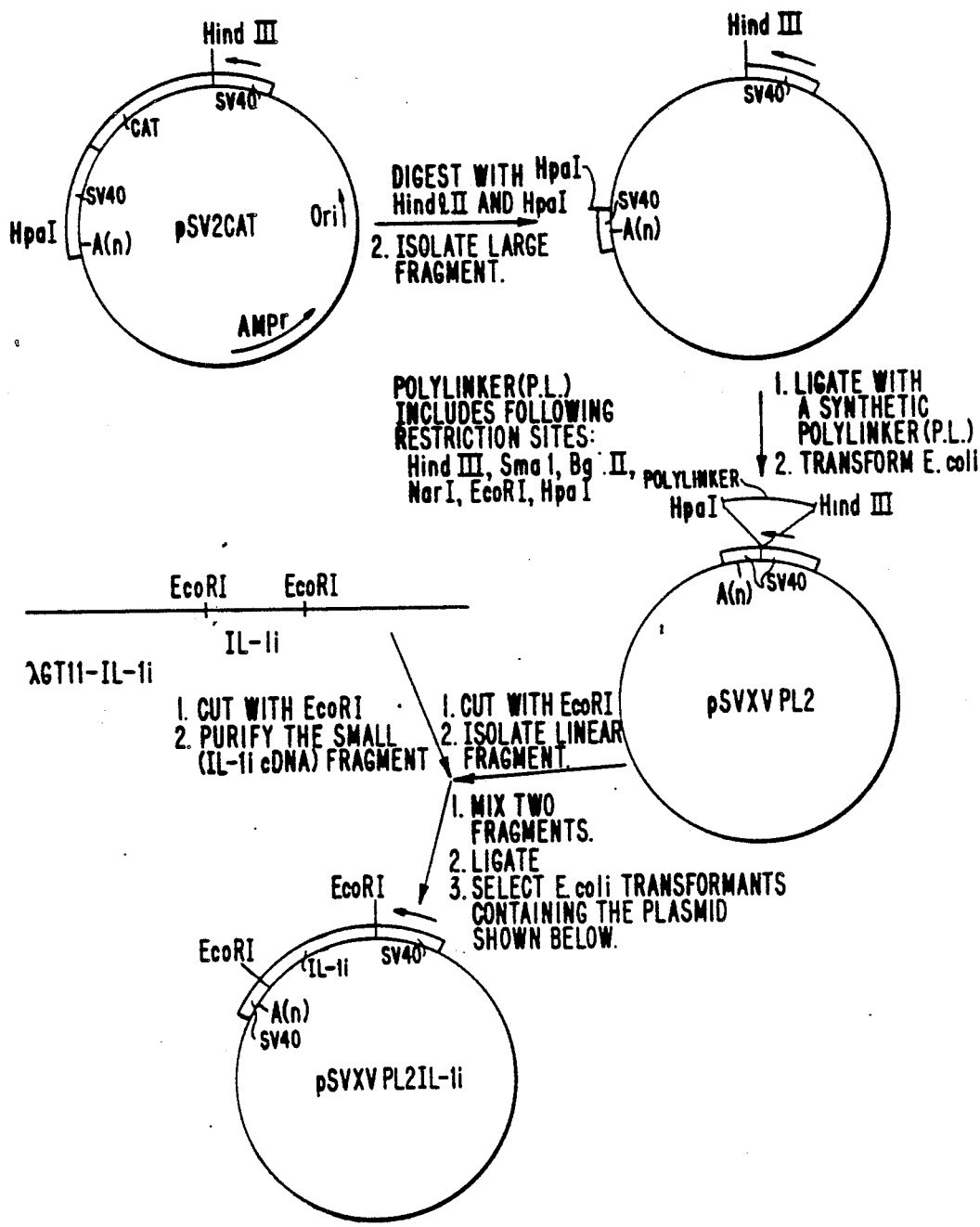
FIG. 6 depicts the construction of plasmid pSVXVPL21L-li.
Figure 7:
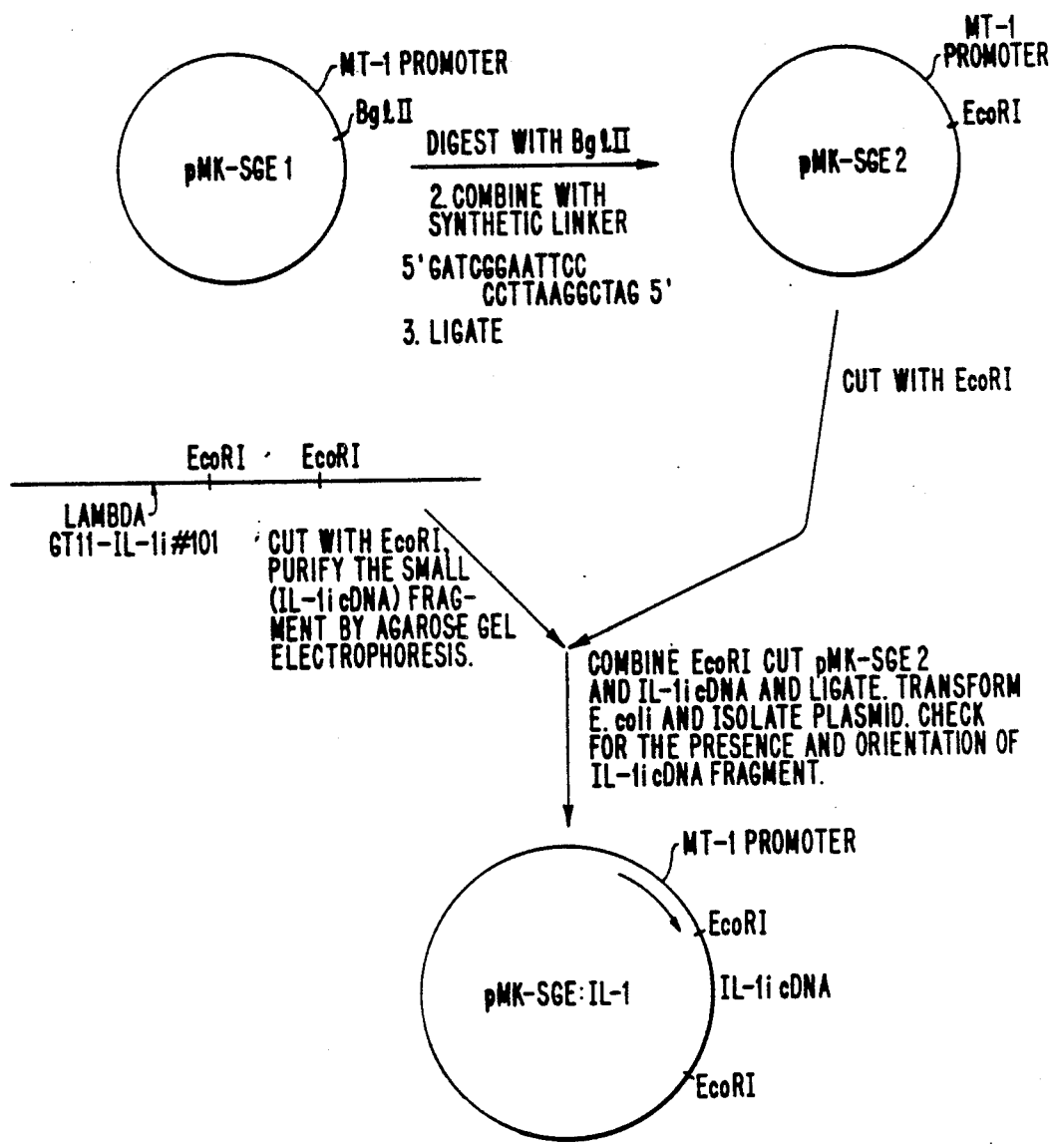
FIG. 7 depicts the construction of plasmid pMK-SGE:IL-li.

Animal-cell expression of IL-li requires the following steps:
 a. Construction of an expression vector
 b. Choice of a host cell line
 c. Introduction of the expression vector into host cells
 d. Manipulation of recombinant host cells to increase expression levels of IL-li 1. IL-li expression vectors designed for use in animal cells can be of several types including strong consitutitve expression constructs, inducible gene constructs, as well as those designed for expression in particular cell types. In all cases promoters and other gene regulatory regions such as enhancers (inducible or not) and polyadenylation signals are placed in the appropriate location in relation to the cDNA sequences in plasmid-based vectors. Two examples of such constructs follow: (1) A construct using a strong constitutive promoter region should be made using the simian virus 40 (SV40) gene control signals in an arrangement such as that found in the plasmid pSV2CAT as described by Gorman et al. in Mol. Cel. Biol. 2:1044–1051, 1982, specifically incorporated herein by reference. This plasmid should be manipulated in such a way as to substitute the IL-li cDNA for the chloramphenicol acetyltransferase (CAT) coding sequences using standard molecular biological techniques (Maniatis et al., supra), as shown in FIG. 6 (2) An inducible gene construct should be made utilizing the plasmid pMK which contains the mouse metallothionein (MT-1) promoter region (Brinster et al., Cell 27:228–231, 1981). This plasmid can be used as a starting material and should be manipulated as shown in FIG. 7 to yield a metal-inducible gene construct.

2. A number of animal cell lines should be used to express IL-li using the vectors described above to produce active protein. Two potential cell lines that have been well-characterized for their ability to promote foreign gene expression are mouse Ltk− and Chinese hamster ovary (CHO) dhfr− cells, although expression of Il-li is not limited to these cell lines.

3. Vector DNA should be introduced into these cell lines using any of a number of gene-transfer techniques The method employed here involves the calcium phosphate-DNA precipitation technique described by S. L. Graham & A. S. van der Eb (Virology 52:456–467, 1973) in which the expression vector for IL-li is co-precipitated with a second expression vector encoding a selectable marker. In the case of Ltk− cell transfection, the selectable marker is a thymidine kinase gene and the selection is as described by Wigler, et al. (Cell 16:777–785, 1979) and in the case of CHO dhfr− cells the selectable marker is dihydrofolate reductase (DHFR) whose selection is as described by Ringold et al. in J. Mol. Appl. Genet. 1:165–175, 1981.

4. Cells that express the IL-li gene constructs should then be grown under conditions that will increase the levels of production of IL-li. Cells carrying the metallothionein promoter constructs can now be grown in the presence of heavy metals such as cadmium which will lead to a 5-fold increased utilization of the MT-1 promoter (Mayo et al., Cell 29:99–108) subsequently leading to a comparable increase in IL-li protein levels. Cells containing IL-li expression vectors (either SV40- or MT-1-based) along with a DHFR expression vector can be taken through the gene amplification protocol described by Ringold et al. (J. Mol. Appl. Genet 1:165–175, 1981) using methotrexate, a competitive antagonist of DHFR. This leads to more copies of the DHFR genes present in the cells and, concomitantly, increased copies of the IL-li genes which, in turn, can lead to more IL-li protein being produced by the cells.

Example 9

Purification of Il-li From Recombinant Animal Cells

Since the IL-li are expected to be secreted from cells like the natural material, it is anticipated that the methods described above for purification of the natural protein will allow similar purification and characterization of the recombinant protein.

Example 10

Sequence of IL-li

The amino terminal residue of IL-li has been identified several times by direct protein sequencing as an arginine (R). The result of such sequencing is shown in Example 3. In contrast, the amino terminal residue of IL-li predicted by the sequence of the cDNA is a proline (P). This amino terminal residue corresponds to nucleotides 85–87 in FIG. 13, and is circled in FIGS. 14 and 15. This apparent disagreement between the cDNA sequence and the direct protein sequence can be resolved by assuming that an error in the cDNA sequence was incorporated during the reverse transcriptase-catalyzed synthesis from its mRNA. That is, a CGA (arginine) codon, located on the mRNA where it would code for that amino terminal residue, could have been changed during the reverse-transcriptase reaction to a CCA (proline) codon in the cDNA. This type of reverse transscriptase problem has been reported in the literature before, e.g., by B. D. Clark et al. in Nucleic Acids Research 14:7897 (1986).

The present inventors believe that the correct amino acid sequence of the protein is as predicted by the cDNA except that the amino terminal amino acid is an arginine instead of the proline residue indicated in FIGS. 13–15. The inventors contemplate that both DNA sequences and their corresponding peptide sequences fall within the scope of their invention although the amino terminal arginine sequence is preferred.

What is claimed is:

1. An isolated DNA sequence encoding a physiologically functional interleukin-1 inhibitor (IL-li) comprising a DNA sequence that is selected from the group consisting of (1) a DNA sequence that encodes IL-li X, IL-li alpha, or IL-li beta and (2) a DNA sequence (i) that cross-hybridizes to a DNA sequence that encodes IL-li X, IL-li alpha, or IL-li beta or (ii) that cross-hybridizes to a DNA sequence that is complementary to a DNA sequence that encodes IL-li X, IL-li alpha, or IL-li beta, wherein said DNA sequence of (i) or (ii) encodes a protein having IL-1 inhibitor activity.

2. The recombinant DNA molecular GT10-ILli-2A.

3. The isolated DNA sequence of claim 1 wherein said DNA sequence comprises a DNA sequence that encodes IL-li X, IL-li alpha or IL-li beta.

4. The isolated DNA sequence of claim 1, wherein said DNA base sequence includes the nucleic acids from position 99 to 554 from the sequence which follows:

```
              70             80             90
CTCTCCTCCTCTTCCTGTTCCATTCAGAGACGATCTG
 T  L  L  L  F  L  F  H  S  E  T  I  C 100            110            120            130
CCCACCCTCTGGGAGAAAATCCAGCAAGATGCAAGCC
 P  P  S  G  R  K  S  S  K  M  Q  A 140            150            160            170
TTCAGAATCTGGGATGTTAACCAGAAGACCTTCTATCT
 F  R  I  W  D  V  N  Q  K  T  F  Y  L 180            190            200            210
GAGGAACAACCAACTAGTTGCTGGATACTTGCAAGGA
 R  N  N  Q  L  V  A  G  Y  L  Q  G 220            230            240
CCAAATGTCAATTTAGAAGAAAAGATAGATGTGGTAC
 P  N  V  N  L  E  E  K  I  D  V  V 250            260            270            280
CCATTGAGCCTCATGCTCTGTTCTTGGGAATCCATGGA
 P  I  E  P  H  A  L  F  L  G  I  H  G 290            300            310            320
GGGAAGATGTGCCTGTCCTGTGTCAAGTCTGGTGATG
 G  K  M  C  L  S  C  V  K  S  G  D 330            340            350
AGACCAGACTCCAGCTGGAGGCAGTTAACATCACTG
 E  T  R  L  Q  L  E  A  V  N  I  T 360            370            380            390
ACCTGAGCGAGAACAGAAAGCAGGACAAGCGCTTCG
 D  L  S  E  N  R  K  Q  D  K  R  F 400            410            420            430
CCTTCATCCGCTCAGACAGTGGCCCCACCACCAGTTTG
 A  F  I  R  S  D  S  G  P  T  T  S  F 440            450            460
AGTCTGCCGCCTGCCCCGGTTGGTTCCTCTGCACA
 E  S  A  A  C  P  G  W  F  L  C  T 470            480            490            500
GCGATGGAAGCTGACCAGCCCGTCAGCCTCACCAATA
 A  M  E  A  D  Q  P  V  S  L  T  N 510            520            530            540
TGCCTGACGAAGGCGTCATGGTCACCAAATTCTACTTC
 M  P  D  E  G  V  M  V  T  K  F  Y  F

↓
       550            560            570
CAGGAGGACGAGTAGTACTGCCCAGGCCTGCTGTT
 Q  E  D  E  *

580            590            600
CCATTCTTGCATGGCAAGGACTG
```

5. The isolated DNA sequence of claim 1, wherein said DNA base sequence includes the nucleic acids from position 99 to 554 from the sequence which follows:

```
              70             80             90
CTCTCCTCCTCTTCCTGTTCCATTCAGAGACGATCTG
 T  L  L  L  F  L  F  H  S  E  T  I  C 100            110            120            130
CCGACCCTCTGGGAGAAAATCCAGCAAGATGCAAGCC
 R  P  S  G  R  K  S  S  K  M  Q  A 140            150            160            170
TTCAGAATCTGGGATGTTAACCAGAAGACCTTCTATCT
 F  R  I  W  D  V  N  Q  K  T  F  Y  L 180            190            200
GAGGAACAACCAACTAGTTGCTGGATACTTGCAAG
 R  N  N  Q  L  V  A  G  Y  L  Q
```

-continued

```
        210       220       230       240
GACCAAATGTCAATTTAGAAGAAAAGATAGATGTGGT
  G  P  N  V  N  L  E  E  K  I  D  V  V 250       260       270       280
ACCCATTGAGCCTCATGCTCTGTTCTTGGGAATCCATG
  P  I  E  P  H  A  L  F  L  G  I  H 290       300       310
GAGGGAAGATGTGCCTGTCCTGTGTCAAGTCTGGT
  G  G  K  M  C  L  S  C  V  K  S  G 320       330       340       350
GATGAGACCAGACTCCAGCTGGAGGCAGTTAACATCA
  D  E  T  R  L  Q  L  E  A  V  N  I 360       370       380       390
CTGACCTGAGCGAGAACAGAAAGCAGGACAAGCGCT
  T  D  L  S  E  N  R  K  Q  D  K  R 400       410       420
TCGCCTTCATCCGCTCAGACAGTGGCCCCACCACCAG
  F  A  F  I  R  S  D  S  G  P  T  T  S 430       440       450       460
TTTTGAGTCTGCCGCCTGCCCCGGTTGGTTCCTCTGCA
  F  E  S  A  A  C  P  G  W  F  L  C 470       480       490       500
CAGCGATGGAAGCTGACCAGCCCGTCAGCCTCACCAA
  T  A  M  E  A  D  Q  P  V  S  L  T  N 510       520       530
TATGCCTGACGAAGGCGTCATGGTCACCAAATTCT
  M  P  D  E  G  V  M  V  T  K  F 540       550   ↓   560       570
ACTTCCAGGAGGACGAGTAGTACTGCCCAGGCCTGCT
  Y  F  Q  E  D  E  *

580       590       600
GTTCCATTCTTGCATGGCAAGGACTG
```

6. The recombinant DNA vector comprising the DNA sequence of claim 1.

7. The vector of claim 6, wherein said vector is an expression vector and further comprises at least one regulatory element needed for the expression of the DNA sequence in a host.

8. The vector of claim 7, wherein said DNA sequence is capable of being expressed in bacteria.

9. The vector of claim 7, wherein said DNA sequence is capable of being expressed in mammalian cells.

10. The vector of claim 6 wherein said DNA sequence comprises a DNA sequence that encodes IL-li X, IL-li alpha or IL-li beta.

11. A cell host including the vector of claim 6 inserted therein.

12. The host cell of claim 11, wherein said host cell is capable of expressing said DNA sequence.

13. The host cell of claim 12, wherein said host cell is a microorganism.

14. The host cell of claim 13, wherein said host cell is a bacterial cell.

15. The host cell of claim 14, wherein said host cell is *Escherichia coli*.

16. The host cell of claim 13, wherein said host cell is a mammalian cell.

17. A recombinant-DNA method for the production of an interleukin-1 inhibitor (IL-li) comprising:
  (a) preparing a DNA sequence encoding a protein having IL-1 inhibitor activity, wherein said DNA sequence is selected from the group consisting of (1) a DNA sequence that encodes IL-li X, IL-li alpha, or IL-li beta and (2) a DNA sequence (i) that cross-hybridizes to a DNA sequence that encodes IL-li X, IL-li alpha, or IL-li beta or (ii) that cross-hybridizes to a DNA sequence that is complementary to a DNA sequence that encodes IL-li X, IL-li alpha, or IL-li beta, wherein said DNA sequence of (i) or (ii) encodes a protein having IL-1 inhibitor activity;
  (b) subcloning the DNA sequence into a vector capable of being inserted into and replicated in a host cell, such vector containing at least one regulatory element needed to express the DNA sequence;
  (c) inserting the vector containing the DNA sequence and at least one regulatory element into a host cell capable of expressing the DNA encoding the IL-1 inhibitor;
  (d) culturing the host cell sunder conditions appropriate for replication of the vector and expression of the IL-1 inhibitor; and
  (e) harvesting the IL-1 inhibitor.

18. The method of claim 17 wherein said DNA sequence comprises a DNA sequence that encodes IL-li X, IL-li alpha or IL-li beta.

19. The method of claim 17 wherein said DNA sequence is a cDNA.

20. The method of claim 17 wherein said DNA sequence is a genomic sequence.

21. The method of claim 17 wherein said DNA sequence is derived from mammalian cells.

22. The method of claim 21 wherein said DNA sequence is derived from human monocytes.

23. The method of claim 17 wherein said host cell is a microorganism.

24. The method of claim 23 wherein said microorganism is *E. coli*.

25. The method of claim 17 wherein said host cells are mammalian cells.

26. The method of claim 25 wherein said mammalian cells are CHO cells.

27. The method of claim 17 wherein said DNA sequence is a synthetic polynucleotide.

28. A recombinant-DNA method for the production of an interleukin-1 inhibitor (IL-li) comprising:
  (a) culturing a host cell that includes inserted therein a vector comprising the DNA sequence of claim 1 operatively linked to at least one regulatory element needed for the expression of the DNA sequence in the host cell;
  (b) harvesting the protein having IL-1 inhibitor activity.

29. A recombinant-DNA method for the construction of an interleukin-1 inhibitor (IL-li) expression vector comprising:
  (a) preparing the DNA sequence of claim 1; and
  (b) subcloning the DNA sequence into a vector capable of being inserted into and replicated in a host cell, such vector containing at least one regulatory element needed for the expression of the DNA sequence.

30. The method of claim 27 wherein said DNA sequence comprises a DNA sequence that encodes IL-li X, IL-li alpha or IL-li beta.

31. The method of claim 28 wherein said DNA sequence comprises a DNA sequence that encodes IL-li X, IL-li alpha or IL-li beta.

* * * * *

UNITED STATES PATENT AND TRADEMARK OFFICE
CERTIFICATE OF CORRECTION

PATENT NO. : 5,075,222

DATED : December 24, 1991

INVENTOR(S) : Charles H. HANNUM et al.

It is certified that error appears in the above-identified patent and that said Letters Patent is hereby corrected as shown below:

Title Page : Item (75) Inventors, line 2, change "Eisenburg" to --Eisenberg--; and line 5, after Colo. insert --; Andreas Sommer of Concord, Calif.--.

(57) Title Page :

line 4, change "inhibitors" to --inhibitor--.

UNITED STATES PATENT AND TRADEMARK OFFICE
CERTIFICATE OF CORRECTION

PATENT NO. : 5,075,222
DATED : December 24, 1991
INVENTOR(S) : Charles H. HANNUM et al.

It is certified that error appears in the above-identified patent and that said Letters Patent is hereby corrected as shown below:

column 1, line 34, change "teneficial" to --beneficial--.

column 2, line 17, after "arteries" insert --.--.

column 4, line 14, change "cf" to --of--.

column 5, line 12, change "pSVXVPL21L-1i" to --pSVXVPL2IL-1i--;

line 57, change "safe" to --same--; and line 59, after "cytes" insert --.--.

column 9, line 11, change "expoited" to --exported--; and line 17, after "invention" insert --.--.

column 10, line 32, --leader sequence must --.

column 12, line 2, change "ar" to --art--; and line 7, after "reference" insert --.--.

column 16, line 50, after "chosen" insert --.--;

line 55, change "(1980)." to --(1980),--; and line 61, after "above" insert --.--.

UNITED STATES PATENT AND TRADEMARK OFFICE
CERTIFICATE OF CORRECTION

PATENT NO. : 5,075,222
DATED : December 24, 1991
INVENTOR(S) : Charles H. HANNUM et al.

It is certified that error appears in the above-identified patent and that said Letters Patent is hereby corrected as shown below:

column 17, line 27, after "inhibitor" insert --.--;
                 line 32, after "herein" insert --.--;
                 line 47, change "o(" to --of--; and
                 line 68, change "preferred.," to --preferred,--.

column 18, line 27, change "3" to --4--; and
                 line 50, change "this" to --these--.

column 19, line 38, change "(HBAA)" to --(HBSS)--; and
                 line 58, change "proliferatirg" to --proliferating--.

column 20, line 9, after "performed" insert --identically except that the plates were coated with fetal calf--;
                 line 11, change "on on" to --on--;
                 line 38, change "Il-li" to --IL-1i--;
                 line 46, change "Il-li" to --IL-1i--; and
                 line 59, after "Kd" insert --.--.

UNITED STATES PATENT AND TRADEMARK OFFICE
CERTIFICATE OF CORRECTION

PATENT NO. : 5,075,222
DATED : December 24, 1991
INVENTOR(S) : Charles H. HANNUM et al.

It is certified that error appears in the above-identified patent and that said Letters Patent is hereby corrected as shown below:

column 21, line 6, after "ways" insert --.--;
               line 9, change "TFA acetonitrile" to --TFA:acetonitrile--;
               line 18, after "sequenced" insert --.--;
               line 39, after "37° C" delete --.--;
               line 42, change "14C-iodcacetic" to --14C-iodoacetic--; and
               line 57, change "IL 1i-h" to --IL-1i-b--.
    column 22, line 18, after "N-termini" insert --.--;
               line 50, after "digestion" insert --.--;
               line 53, change "Plus.," to --Plus),-- and
               line 60, change "SDS-pAGE" to --SDS-PAGE--.
    column 23, line 3, after "37° C" delete --.--;
               line 44, after "37° C" delete --.--;
               line 46, after "37° C" delete --.--; and
               line 47, after "dark)" insert --.--.
    column 24, line 1, after "pumps" insert --.--.
    column 26, line 43, change "ratiolabelled" to --radiolabelled--.

UNITED STATES PATENT AND TRADEMARK OFFICE
CERTIFICATE OF CORRECTION

PATENT NO. : 5,075,222

DATED : December 24, 1991

INVENTOR(S) : Charles H. HANNUM et al.

It is certified that error appears in the above-identified patent and that said Letters Patent is hereby corrected as shown below:

```
       column 27, line 26, after "column" insert --.--;
                  line 33, change "oligonucleotde" to
--oligonucleotide--; and
                  line 68, after "40488" insert --.--.
       column 28, line 17, after "ods" insert --.--.
       column 29, line 53, after "here" insert --.--; and
                  line 67, change "is" (second occurrence) to
--this--.
       column 30, line 31, after "FIG. 6" insert --.--; and
                  line 47, after "techniques" insert --.--.
```

IN THE CLAIMS:

Claim 2, column 31, line 62, change "molecular" to --molecule--.

Claim 6, column 33, line 39, change "The" to --A--.

UNITED STATES PATENT AND TRADEMARK OFFICE
CERTIFICATE OF CORRECTION

PATENT NO. : 5,075,222

DATED : December 24, 1991

INVENTOR(S) : Charles H. HANNUM ET AL.

It is certified that error appears in the above-indentified patent and that said Letters Patent is hereby corrected as shown below:

Claim 17, column 34, line 18, change "sunder" to --under--.

Signed and Sealed this

Seventh Day of March, 1995

Attest:

BRUCE LEHMAN

*Attesting Officer*  *Commissioner of Patents and Trademarks*